(12) United States Patent
Sone et al.

(10) Patent No.: US 7,025,964 B1
(45) Date of Patent: Apr. 11, 2006

(54) PEPTIDE-BASED IMMUNOTHERAPEUTIC AGENT

(75) Inventors: Toshio Sone, Kanagawa (JP); Akinori Kume, Kanagawa (JP); Kazuo Dairiki, Kanagawa (JP); Kohsuke Kino, Kanagawa (JP)

(73) Assignee: Meiji Dairies Corporation, Tokyo (JP)

( * ) Notice: Subject to any disclaimer, the term of this patent is extended or adjusted under 35 U.S.C. 154(b) by 0 days.

(21) Appl. No.: 09/308,027

(22) PCT Filed: Nov. 12, 1997

(86) PCT No.: PCT/JP97/04129

§ 371 (c)(1),
(2), (4) Date: Aug. 16, 1999

(87) PCT Pub. No.: WO98/20902

PCT Pub. Date: May 22, 1998

(30) Foreign Application Priority Data

Nov. 13, 1996 (JP) ............................................. 8-302053

(51) Int. Cl.
*A61K 39/36* (2006.01)
*C07K 7/00* (2006.01)

(52) U.S. Cl. ............................... 424/185.1; 424/275.1; 530/326

(58) Field of Classification Search ............... 424/185.1, 424/275.1; 435/7.92, 7.21; 530/300, 326
See application file for complete search history.

(56) References Cited

FOREIGN PATENT DOCUMENTS

| EP | 0432691 A1 | 6/1991 |
|---|---|---|
| EP | 0700929 A2 | 3/1996 |
| EP | 0700929 A3 | 3/1996 |
| JP | 7-118295 A | 5/1995 |

(Continued)

OTHER PUBLICATIONS

Hashiguchi et al. Molecular immunology of Japanese cedar pollen allergens: analysis of T cell epitopes, Aug. 1996, Nippon Rinsho 54(8): 2233–42.*
Hori et al, Janpanese cedar pollinosis and HLA–DP5, Jun. 1996, Tissue Antigens 47(6): 485–91.*
Hoyne et al, Immunology and Cell Biology 74: 180–186, 1996.*
Briner et al., Peripheral T–cell tolerance included in naïve and primed mice by subcutaneous injection of peptides from the major cat allergen Fel d I, Proc. Natl. Acad. Sci. USA 90:7608–7612, Aug. 1993.
O'Hehir et al., "The Specificity and Regulation of T–Cell Responsiveness to Allergens," Annu. Rev. Immunol. 9:67–95, 1991.
Rogers et al., "Potential Therapeutic Recombinant Proteins Comprised of Peptides Containing Recombined T Cell Epitopes," Molecular Immunology 31(13): 955–966, 1994.

Higgins et al., "Overlapping T–cell epitopes in the group 1 allergen of Dermatophagoides species restricted by HLA–DP and HLA–Dr class II molecules," J Allergy Clin. Immunol. 93:891–9, 1994.
Matsunaga et al., "Participation of cathepsin B in processing of antigen presentation to MHC class II," FEBS Letters 324(3):325–330, 1993.
Ishikawa et al., "Human T. Cell Response to Antigen Peptides of Japanese Cedar Pollen (Cry j 1)," Int. Arch. Allergy Immunol. 113:255–257, 1997.
Dodson, "Counting dinosaurs: How many kinds were there?," Proc. Natl. Acad. Sci., USA, 87: 7608–7612, 1990.
Hashimoto et al., "Sensitivity to two major allergens (Cry j I and Cry j II) in patients with Japanese cedar (*Cryptomeria japonica*) pollinosis," Clinical and Experimental Allergy 25:848–852, 1995.
Hori et al., "Japanese cedar pollinosis and HLA–DP5," Tissue Antigens 47:485–491, 1996.
Ikagawa et al., "Allergens, IgE, mediators, inflammatory mechanisms—Single amino acid substitutions . . . antagonism," J. Allergy Clin. Immunol. 97:53–64, 1996.
June et al., "The B7 and CD28 receptor families," Immunology Today 15(7):321–331, 1994.
Komiyama et al., "cDNA cloning and Expression of Cry j II, the Second Major Allergen of Japanese Cedar Pollen," Biochemical and Biophysical Research Communications 201(2):1021–1028, 1994.
Matsushita et al., "Allele Specificity of Structural Requirement for Peptides Bound to HLA–DRB1*0405 and – DRB1*0406 Complexes . . . Syndrome," J. Exp. Med. 180:873–883, 1994.
Rammensee et al., "MHC ligands and peptide motifs: first listing," Immunogenetics 41:178–228, 1995.
Sasazuki et al. in *DNA Component*, vol. 1, pp. 395–518, 1982.
Yasueda et al., "Isolation and partial characterization of the major allergen from Japanese cedar (*Cryptomeria japonica*) pollen," J. Allergy Clin. Immunol. 71(No. 1, Part 1):77–86, 1983.

*Primary Examiner*—Christina Chan
*Assistant Examiner*—Phuong N Huynh
(74) *Attorney, Agent, or Firm*—Fish & Richardson P.C.

(57) ABSTRACT

A peptide-based immunotherapeutic agent effective for every allergy patient is provided. A reagent for typing HLA class II molecules of the patient to be used in selecting a peptide-based immunotherapeutic agent effective for every allergy patient is also provided. The peptide-based immunotherapeutic agent enables the optimal peptide-based immunotherapy for each patient, so that a marked improvement in peptide-immunotherapy can be expected. The peptide-based immunotherapeutic agent is also effective for patients who cannot be treated by peptide-based immunotherapy using major antigen peptide recognized in a particular patient population. Furthermore, the peptide-based immunotherapeutic agent enables simple and easy typing of HLA class II molecules of allergy patients.

2 Claims, 8 Drawing Sheets

FOREIGN PATENT DOCUMENTS

| | | |
|---|---|---|
| JP | 8-047392 A | 2/1996 |
| JP | 8-333391 A | 12/1996 |
| WO | WO 93/01213 | 1/1993 |
| WO | WO 93/08279 | 4/1993 |
| WO | WO 94/01560 | 1/1994 |
| WO | WO 94/11738 A1 | 5/1994 |
| WO | WO 94/16068 | 7/1994 |
| WO | WO 97/32600 | 9/1997 |

* cited by examiner

TH TYPE OF T CELL CLONE CAPABLE OF RECOGNIZING CRY J 1

| T CELL CLONE | EPITOPE SITE NO. | EPITOPE SITE POSITION | RESTRICTION MOLECULE | LYMPHOKINE PRODUCTION (pg/ml) IL-2 | IFNγ | IL-4 | Th* TYPE |
|---|---|---|---|---|---|---|---|
| PJ4-6 | 4 | 16-30 | DQA1*0102 DQB1*0602 | <31 | 1500 | 334 | Th0 |
| PB8-1 | 4 | 16-30 | DQA1*0102 DQB1*0602 | <31 | <31 | 814 | Th2 |
| PB9-37 | 13 | 61-75 | DPA1*0101-DPB1*0501 | <31 | <31 | 7760 | Th2 |
| PB10-24 | 13 | 61-75 | DPA1*0101-DPB1*0501 | 39 | 151 | 4500 | Th2 |
| PJ1-27 | 19 | 91-105 | DQ | 32 | 1220 | 224 | Th0 |
| PB3-27 | 22 | 106-120 | DRB5*0101 | 250 | 332 | 21000 | Th2 |
| PB8-2 | 22 | 106-120 | DRB5*0101 | 190 | 2110 | 5709 | Th0 |
| PB8-3 | 22 | 106-120 | DRB5*0101 | <31 | 1270 | 10100 | Th0 |
| PB9-39 | 22 | 106-120 | DRB5*0101 | 48 | 51 | 5120 | Th2 |
| PB10-18 | 22 | 106-120 | DRB5*0101 | 410 | 46 | 7840 | Th2 |
| PJ4-29 | 22 | 106-120 | DRB5*0101 | 4680 | 14200 | 6610 | Th0 |
| PJ7-9 | 22 | 106-120 | DRB5*0101 | 1370 | 1040 | 12200 | Th2 |
| PJ5-6 | 30 | 146-160 | DQA1*0102-DQB1*0602 | 1500 | 1170 | 5920 | Th0 |
| PJ5-9 | 30 | 146-160 | DQA1*0102-DQB1*0602 | 1720 | 825 | 266 | Th0 |
| PB11-21 | 31 | 151-165 | DRB1*0901 | 4190 | >20000 | 4510 | Th0 |
| PB11-24 | 31 | 151-165 | DRB1*0901 | 670 | 11700 | 1950 | Th0 |
| PB6-37 | 31 | 151-165 | DRB1*0901 | <31 | <31 | 49 | Th2 |
| PB1-8 | 39 | 191-205 | DQA1*0102-DQB1*0602 | 820 | 188 | 1760 | Th0 |
| PB9-34 | 39 | 191-205 | DRB1*0901 or DRB4*0101 | <31 | 86 | 1680 | Th2 |
| PB2-14 | 43 | 211-225 | DPA1*0101-DPB1*0501 | <31 | 376 | 2320 | Th0 |
| PB7-2 | 43 | 211-225 | DPA1*0101-DPB1*0501 | 84 | 2740 | 2080 | Th0 |
| PB8-32 | 43 | 211-225 | DPA1*0101-DPB1*0501 | <31 | 4870 | 1840 | Th0 |
| PB8-34 | 43 | 211-225 | DPA1*0101-DPB1*0501 | 78 | 14800 | 3040 | Th0 |
| PB11-23 | 43 | 211-225 | DPA1*0101-DPB1*0501 | <31 | 3990 | 1260 | Th0 |
| PB11-26 | 43 | 211-225 | DPA1*0101-DPB1*0501 | 32 | 1100 | 6520 | Th0 |
| PB4-20 | 43 | 211-225 | DPA1*0101-DPB1*0501 | <31 | <31 | 133 | Th2 |
| PB10-4 | 43 | 211-225 | DPA1*0101-DPB1*0501 | <31 | <31 | 4170 | Th2 |
| PB8-4 | 51 | 251-265 | DQA1*0102-DQB1*0602 | 44 | 36 | 4050 | Th2 |
| PJ4-20 | 66 | 326-340 | DQA1*0102-DQB1*0602 | 560 | 3080 | <32 | Th1 |

FIG. 3

TH TYPE OF T CELL CLONE CAPABLE OF RECOGNIZING CRY J 2

| T CELL CLONE | EPITOPE SITE NO. | EPITOPE SITE POSITION | RESTRICTION MOLECULE | LYMPHOKINE PRODUCTION (pg/ml) IL-2 | LYMPHOKINE PRODUCTION (pg/ml) IFNγ | LYMPHOKINE PRODUCTION (pg/ml) IL-4 | Th* TYPE |
|---|---|---|---|---|---|---|---|
| PB5-29 | 4 | 16-30 | DRB1*0901 or DRB4*0101 | <31 | 503 | 97 | Th0 |
| PB11-40 | 4 | 16-30 | DRB1*0901 or DRB4*0101 | <31 | <31 | 50 | Th2 |
| PB14-4 | 4 | 16-30 | DRB1*0901 or DRB4*0101 | <31 | <31 | <16 | Thp |
| PB12-33 | 8 | 36-50 | DRB1*1501 | <31 | >8000 | <16 | Th1 |
| PR2-25 | 8 | 36-50 | DRB1*1501 | 47 | <31 | 977 | Th2 |
| PR5-40 | 8 | 36-50 | DRB1*1501 | 1150 | 1330 | 355 | Th0 |
| PB3-32 | 14 | 66-80 | DRB5*0101 | <31 | <31 | 323 | Th2 |
| PB4-21 | 14 | 66-80 | DRB5*0101 | <31 | 109 | 239 | Th0 |
| PB4-22 | 14 | 66-80 | DRB5*0101 | <31 | 483 | 158 | Th0 |
| PC1-8 | 14 | 66-80 | DRB5*0101 | <31 | 2710 | 32 | Th1 |
| PR4-20 | 14 | 66-80 | DRB5*0101 | <31 | 312 | 338 | Th0 |
| PR3-21 | 14 | 66-80 | DRB5*0101 | <31 | <31 | 338 | Th2 |
| PB13-18 | 17 | 76-90 | DPA1*0101-DPB1*0501 | <31 | 3320 | 231 | Th1 |
| PB11-32 | 17 | 76-90 | DPA1*0101-DPB1*0501 | 138 | 60 | 2090 | Th2 |
| PR1-20 | 31 | 151-165 | DRB1*0901 | <31 | <31 | 18 | Th2 |
| PR4-39 | 31 | 151-165 | DRB1*0901 | <31 | <31 | <16 | Thp |
| PB14-5 | 37 | 181-195 | DPA1*0101-DPB1*0201 | 87 | 126 | 469 | Th0 |
| PB14-13 | 37 | 181-195 | DPA1*0101-DPB1*0201 | <31 | 59 | 2440 | Th2 |
| PB14-34 | 38 | 186-200 | DRB4*0101 | 186 | 420 | 93 | Th0 |
| PC3-40 | 38 | 186-200 | DRB4*0101 | <31 | <31 | 379 | Th2 |
| PB5-3 | 48 | 236-250 | DRB1*1501 or DRB5*0101 | 2570 | >8000 | 525 | Th1 |
| PR2-34 | 65 | 321-335 | DRB1*0901 | 57 | 1990 | 464 | Th0 |
| PR3-30 | 66 | 326-340 | DQA1*0102-DQB1*0602 | <31 | 106 | <80 | Th1 |
| PR5-18 | 66 | 326-340 | DQA1*0102-DQB1*0602 | <31 | <31 | <16 | Thp |
| PC1-13 | 68 | 336-350 | DPA1*0202-DPB1*0501 | <31 | <31 | <16 | Thp |
| PB12-8 | 69 | 341-355 | DQA1*0102-DQB1*0602 | <31 | 3210 | <16 | Th1 |
| PR5-12 | 69 | 341-355 | DQA1*0102-DQB1*0602 | <31 | <31 | 2528 | Th2 |
| PR2-31 | 69 | 341-355 | DQA1*0102-DQB1*0602 | <31 | <31 | 332 | Th2 |
| PB14-19 | 70 | 346-360 | DQA1*0102-DQB1*0602 | <31 | 3730 | <16 | Th1 |
| PB13-38 | 70 | 346-360 | DQA1*0102-DQB1*0602 | <31 | 2020 | <16 | Th1 |

FIG. 4

PEPTIDE-BASED IMMUNOTHERAPEUTIC AGENT

This application claims priority of International Application No. PCT/JP97/04129, filed Nov. 12, 1997, which claims priority of Japanese Application No. 8/302053, filed Nov. 13, 1996.

TECHNICAL FIELD

The present invention relates to a peptide-based immunotherapeutic agent. More specifically, the present invention relates to a peptide-based immunotherapeutic agent useful for an allergy patient who has HLA class II molecules that bind to a specific antigen peptide derived from an allergen, which comprises a specific antigen peptide as an effective ingredient. Furthermore, the present invention relates to a reagent for identifying HLA class II molecules, which comprises an antigen peptide specifically reacting with specific HLA class II molecules.

BACKGROUND ART

An allergic reaction is an undesirable immunoreaction resulting from the response of an antibody or a sensitized cell to an antigen. An antigen causing an allergic reaction is specifically called an allergen. Allergens include a wide range of substances, such as pollen, mites, animals' epidermis, insects, foods, drugs, and chemicals. An allergic reaction is generally characterized by a two-phase reaction comprising an immediate reaction to an allergen and a subsequent delayed reaction. In the early stage of an allergic reaction, an allergen-specific IgE antibody binds to the surface of basophils in the peripheral blood and mast cells in tissues. When an allergen enters the body, the IgE antibodies on the surface of basophils or mast cells cross react with the allergen. As a result, inflammatory mediators including histamine, prostaglandin, and leukotriene are released. In response to these inflammatory mediators, locally accumulated lymphocytes, monocytes, basophils, and eosinophils are activated and release mediators causing tissue damage and other various responses in tissues, thereby initiating a delayed reaction.

It is well known that an allergic reaction is controlled by cytokines. Cytokines are involved in not only the control of IgE production but also the activation and differentiation of effector cells. This is supported by the observation that the level of an allergen-specific IgE in the blood is constant even if clinical symptoms of an allergy patient have been alleviated by hyposensitization.

Hyposensitization, a method for treating allergic diseases, comprises administering a small amount of antigen (for example, an antigen extracted from cryptomeria pollen or mites) to an allergy patient, and increasing the dosage gradually. The success of hyposensitization is attributed to the decreased response of allergen-specific T cells. Presumedly, hyposensitization causes T-cell tolerance (T cell anergy), and, as a result, cytokine, which is important for developing an allergic cascade, is not produced. Studies on allergies have focused on the allergen-specific immunoreaction in the early stage, especially on the mechanisms for controlling T-cell response to allergy. An allergic response to an exogenous antigen including an allergen is initiated depending on antigen-presenting cells in the immune system. Antigen-presenting cells, including B cells, macrophages, and dendritic cells, incorporate exogenous antigens, fragment the exogenous antigens into antigen peptides (T-cell epitope peptides), and express the fragmented antigens on the cell surface together with MHC class II (HLA class II for a human) to present an antigen to antigen-specific CD4 positive helper T cells (Th cells).

HLA class II molecules (DR, DQ, and DP) are cell surface antigens composed of α and β chains. The α chain of the DR molecule is encoded by the HLA-DRA gene; the β chain of the DR molecule is encoded by HLA-DRB1, HLA-DRB3, HLA-DRB4, or HLA-DRB5 genes. The α and β chains of the DQ molecule are encoded by HLA-DQA1 and HLA-DQB1 genes, respectively, while α and β chains of the DP molecule are encoded by HLA-DPA1 and HLA-DPB1 genes, respectively. Except for HLA-DRA, each gene comprises numerous alleles. Pockets accommodating antigen peptides composed of α and β chains show high polymorphism, and their structures differ slightly from each other. As a result, kinds of antigen peptides binding to pockets and presented to T cells are limited by their structure. This presumably produces differences in individual immunoreactions.

Th cells that receive the antigenic information restricted by HLA class II molecules through T-cell receptors (TCR) are activated and secrete various cytokines to proliferate by themselves and differentiate B cells into plasma cells, thereby inducing antibody production. At this time, the second signal (costimulatory signal), which is mediated by molecules other than TCR, is necessary to activate T cells. In contrast, without this signal, immunological tolerance of Th cells to an antigen is induced (June, C. et al.: Immunol Today, 15: 321, 1994).

The decrease of T-cell response to an allergen is related to the success of hyposensitization. For example, the T-cell response in vitro to ambrosia allergen "Amb a 1" in a patient suffering from an ambrosia allergy who had undergone effective hyposensitization for ten years was dramatically decreased compared to an untreated patient. Similarly, in a patient allergic to feline epidermis antigen "Fel d 1," T-cell response specific to Fel d 1 was obviously decreased, as hyposensitization showed effects. This decrease corresponded to the decrease of sensitivity in the skin test. Furthermore, IgG and IgE antibodies specific to Fel d 1 remained at a constant level during the treatment. These results indicated that a therapeutic agent for an allergy directly targeting antigen-specific T cells could be prepared.

Development of biochemical separation and analysis techniques has enabled purification of various allergens. In particular, more than 100 kinds of allergen genes have been cloned and their primary structures have been determined in the last several years using techniques in molecular biology and genetic engineering. T-cell epitope sites were also identified in some of those allergens.

Peptide-based immunotherapeutic compositions using peptides including T-cell epitopes of allergens have been disclosed (International patent application published in Japan Nos. Hei 7-502890, Hei 8-502163, and Hei 8-507436). When some parts of a T-cell epitope of feline allergen Fel d 1 molecule, but not all of it, were subcutaneously administered to a mouse, antigen-specific T-cell tolerance was reportedly induced against the challenge of whole Fel d 1 (Briner, T. J. et al.: Proc. Natl. Acad. Sci. USA, 90: 7608–7612, 1994). However, whether a major T-cell epitope is effective enough to decrease T-cell response to the challenge of a whole allergen and whether this is can alleviate clinical symptoms have not been confirmed by clinical experiments in humans.

Reportedly, about 3 to 16 T-cell epitope sites exist in an allergen molecule, of which about 1 to 7 sites are recognized by a patient. When the HLA class II type differs in each patent, T-cell epitope sites recognized by each patient also differ. When the HLA class II type is the same, the same T-cell epitope sites are recognized. Thus, the above-described peptide-based immunotherapy using a peptide containing only one major epitope of an allergen molecule recognized in a particular patient population cannot be effective for all patients.

DISCLOSURE OF THE INVENTION

An objective of the present invention is to provide a peptide-based immunotherapeutic agent effective for individual allergy patients. Another objective of the present invention is to provide a reagent for typing HLA class II molecules of a patient to be used for selecting a peptide-based immunotherapeutic agent effective for individual allergy patients.

The present inventors focused on the fact that each patient recognizes different T-cell epitopes of an allergen. The inventors established a method for correlating various T-cell epitopes of allergic molecules with types of the patient's HLA class II molecule that restrict the epitopes. They actually correlated various T-cell epitopes of allergen molecules with types of patient's HLA class II molecules restricting the epitopes in cryptomeria pollen allergens, Cry j 1 and Cry j 2 as follows.

Based on the known HLA-binding motifs of DR, DQ and DP (Rammensee, H. G. et al.: Immunogenet. 41: 178–228, 1995), T-cell epitope sites of allergen molecules can be determined by analyzing the primary structure of allergen molecules and detecting the existence of HLA motifs. Therefore, in order to maximize the possibility that T-cell epitope sites are contained in peptides to be constructed, the epitope sites should be estimated based on known HLA-binding motifs, and peptides should be constructed using said estimated motifs. However, peptides containing estimated HLA motifs do not always cause the expected allergic symptoms. Antigen peptides useful for peptide-based immunotherapy must be determined at least by an experiment using T cells (peripheral blood lymphocytes, T cell lines or T-cell clones). The present inventors identified antigen peptides useful for peptide-based immunotherapy for each HLA type by such an experiment.

The present inventors cultured peripheral lymphocytes, T-cell lines, or T-cell clones derived from a patient sensitive to a specific allergen with antigen-presenting cells and overlapping peptides composed of about 15 to 30 amino acid residues (in which the overlapping portion is about 5 to 10 residues) to cover the whole primary structure of the allergen. T-cell response to these peptides was then assayed by measuring the amount of [$^3$H]thymidine uptake (response by cell proliferation). The peptides to which T-cells responded were identified as antigen peptides containing at least one T-cell epitope. Subsequently, the inventors successfully correlated other T-cell epitopes with the patient's HLA class II molecules that restrict the epitopes using various T-cell lines or T cell clones.

Furthermore, the inventors identified T-cell epitopes recognized by a specific mouse. The inventors found that the same mouse which was given said T-cell epitopes exhibited significantly suppressed immune response to the peptides containing said T-cell epitopes. Based on this result, the inventors thought that a peptide-based immunotherapeutic agent effective for individual patients could be provided by selecting T-cell epitope peptides compatible to a type of HLA class II molecule specific to the patient from peptides containing T-cell epitope for which restriction molecules were identified, thereby completing the present invention.

Furthermore, specific T-cell epitopes binding to specific HLA class II molecules can be detected by the method of the present invention. The present inventors considered using the specific T-cell epitopes as a reagent for typing the patient's HLA class II molecules and completed the present invention. The reagent for typing the HLA class II molecules can be effectively used for selecting a peptide-based immunotherapeutic agent effective for individual patients.

Specifically, the present invention consists of the inventions described in each claim.

The terms used herein are defined as follows.

"T-cell epitope" means a structure recognized (or responded to) specifically by a T-cell receptor.

Epitopes that are "recognized" are epitopes that activate T cells. Whether T cells are activated or not can be observed by the production of cytokines, such as IL-2, IL-4 and IFN-γ or by DNA synthesis.

"Antigen peptide" means a peptide functioning as an antigen and containing T-cell epitopes.

"Anergy" means a status in which lymphocytes are not activated by antigens and are functionally inactive.

"HLA haplotype" means the combination of HLA class gene loci that are normally inherited as a particular group.

"Linkage disequilibrium" means the correlation found among different genes when alleles of different HLA loci are present in a single chromosome or a haplotype with higher frequency than expected by chance. Linkage disequilibrium is quantified by the difference between the expected and observed values (Δ).

Peptides binding to specific HLA molecules normally contain specific amino acid residues at specific sites. "HLA-binding amino acid motif" means the combination of the sites and kinds of amino acid residues (HLA anchor residues) important for binding to HLA molecules on HLA-binding peptides. Each HLA allele product contains its own motif. An HLA-binding amino acid motif is also simply referred to as an HLA-binding motif herein.

In the present invention, T-cell epitopes in an allergen molecule can be mapped by, for example, culturing peripheral blood lymphocytes, T-cell lines, or T-cell clones derived from a patient sensitive to a specific allergen, together with antigen-presenting cells and an overlapping peptide composed of about 15 to 30 amino acid residues (in which the overlapping portion is about 5 to 10 residues) which covers the whole primary structure of said allergen, determining T-cell response to these peptides by measuring the amount of [$^3$H]thymidine uptake (response by cell proliferation), and identifying the peptide to which T-cells responded. The exact epitope sites can be identified by synthesizing deletion variant peptides by deleting amino or carboxyl terminal amino acid residues of antigen peptides and monitoring the change of T-cell response to these variant peptides. Alternatively, when more than two peptides containing overlapping regions produce T-cell responses, the exact epitope sites can be identified by synthesizing new T-cell epitope peptides containing a part or all of the overlapping regions, and monitoring the change of T-cell response. The antigen peptide of the present invention preferably contains at least seven amino acid residues.

T-cell response to antigen peptides can be detected by calculating the stimulation index (SI) which indicates the level of T-cell response to antigen peptides. SI can be calculated by dividing the value (cpm) of [$^3$H]thymidine uptake in response to the peptide by the value (cpm) obtained by using the medium without the peptide. The SI of an antigen peptide useful for peptide-based immunotherapy of the invention is at least 2.0, preferably at least 2.5, more preferably at least 3.5, and most preferably, at least 5.0.

An antigen peptide of the present invention induces proliferation in vitro in peripheral blood lymphocytes. T-cell lines or T-cell clones derived from an individual allergy patient having HLA class II molecules restricting said peptide. An antigen peptide of the invention does not react with an IgE antibody of a patient sensitive to the allergen from which said peptide is derived. The antigen peptide of the present invention can induce antigen-specific T-cell anergy by the administration of the antigen peptide and thereafter can induce immunological tolerance at any time when challenge with a recombinant or natural allergen derived from said antigenic peptide is made. Furthermore, once an antigen peptide of the present invention is administered to an individual sensitized by an allergen, immunological tolerance in the individual can be induced at any time thereafter by challenging with said allergen. These facts indicate that the antigenic peptide of the present invention induces an antigen-specific immunological tolerance in vitro and is useful for peptide-based immunotherapy of an allergy patient.

HLA class II molecules of an allergy patient which bind to the antigen peptides can be typed as follows. Identified antigen peptides, self-derived EB lines treated with mitomycin C (B-cell strains transformed by Epstein-Barr virus), and T cells are cultured with anti-HLA-DR antibody, anti-HLA-DQ antibody, or anti-HLA-DP antibody to assay the inhibition of T-cell proliferation response, thereby identifying which of molecules DR, DQ or DP restricts the antigen peptide. When identified restriction molecules are either DQ or DP, the type of restriction molecule (DQ or DP) can be identified using EB lines with a known HLA haplotype as antigen-presenting cells (Hori, T. et al.: Tissue Antigen 47: 485–491, 1996). HLA class II DNA typing is performed by extracting DNA from B-cell lines and subjecting it to the PCR-SSO method adopted in the 11th International Major Histocompatibility Conference [Tsuji, K., Aizawa, M. & Sashazwuki, T eds, (1982) HLA-1991 vol. 1 pp 395–518]. Restriction molecule DR cannot be identified by using EB lines as antigen-presenting cells due to linkage disequilibrium between DRB1* and DR super types (DRB3*, DRB4*, and DRB5*). Therefore, restriction molecules are identified by transforming mouse L-cell with DRB1* or only one type of DR super type and using the transformant expressing the introduced gene as antigen-presenting cells.

Examples of antigen peptides and the HLA class II molecules restricting them are as follows.

At present, major allergens of cryptomeria pollen allergen, Cry j 1 and Cry j 2, have been isolated and purified. cDNAs of both allergens have been isolated, and their estimated primary structures have been disclosed (International patent application published in Japan Nos. Hei 8-502163 and Hei 8-505284). T-cell epitope sites in the Cry j 1 molecule were identified based on the molecule's primary structure. A therapeutic composition for cryptomeria pollen allergy, composed of a peptide containing the epitope site as an effective ingredient, has been disclosed (International patent application published in Japan No. Hei 8-502163). It was reported that more than 90% of patients suffering from a cryptomeria pollen allergy have IgE antibodies specific to Cry j 1 and to Cry j 2; the remaining 10% of patients have IgE antibody specific to either Cry j 1 or Cry j 2 (Hashimoto, M et al. Clin. Exp. Allergy 44: 840–841, 1995).

Based on the above report, the present inventors thought that peptide-based immunotherapy by administering either Cry j 1 T-cell epitopes or Cry j 2 T-cell epitopes would not be sufficiently effective. The present inventors provided multiple epitope peptides with the minimum length effective for peptide-based immunotherapy to a cryptomeria pollen allergy caused by antigen peptides presented by HLA-DPB1*0501. HLA-DPB1*0501 is frequently present in patients suffering from Cryptomeria pollen allergy induced by Cry j 1 and Cry j 2, and antigen peptides presented by different HLA class II molecules (DR, DQ or DP) (Japanese Patent Application No. Hei 8-80702).

This multiple epitope peptide can be expected to have enhanced effectiveness in allergy patients but is ineffective for patients who do not have HLA molecules restricting an antigen peptide composed of said epitope peptides. An antigen peptide compatible with an individual HLA type should be administered to the individual for effective peptide-based immunotherapy.

Examples of combinations of the antigen peptides with types of HLA class II restriction molecules in patients suffering from a cryptomeria pollen allergy are given below. Specific examples of HLA class II molecules and their binding partner antigen peptides include:

1) DRB5*0101 of a patient suffering from a cryptomeria pollen allergy, binds to antigen peptides p106–120 (SEQ ID NO: 3) and p109–117 (SEQ ID NO: 4) derived from Cry j 1, and antigen peptides p66–80 (SEQ ID NO: 14) and 236–250 (SEQ ID NO: 19) derived from Cry j 2, 2) DRB4*0101 binds to antigen peptides p191–205 (SEQ ID NO: 7) derived from Cry j 1 and antigen peptides p16–30 (SEQ ID NO: 12) and p186–200 (SEQ ID NO: 18) derived from Cry j 2.

3) DQA1*0102-DQB1*0602 binds to antigen peptides p16–30 (SEQ ID NO: 1), p146–160 (SEQ ID NO:5), p191–205 (SEQ ID NO: 7), p251–265 (SEQ ID NO: 9), and p326–340 (SEQ ID NO: 10) derived from Cry j 1 and antigen peptides p326–340 (SEQ ID NO: 21), p341–355 (SEQ ID NO: 23), and p346–360 (SEQ ID NO: 142) derived from Cry j 2.

4) DPA1*0101-DPB1*0501 binds to antigen peptides p61–75 (SEQ ID NO: 2) and 211–255 (SEQ ID NO: 8) derived from Cry j 1 and antigen peptide p76–90 (SEQ ID NO: 15) derived from Cry j 2.

5) DPA1*0202-DPB1*0501 binds to antigen peptide p336–350 (SEQ ID NO: 22) derived from Cry j 2, 6) DPA1*0101-DPB*201 binds to p181–195 (SEQ ID NO: 17) derived from Cry j 2, 7) DRB1*0901 binds to antigen peptides p151–165 (SEQ ID NO: 6) and p191–205 (SEQ ID NO: 7) derived from Cry j 1, and antigen peptides 16–30 (SEQ ID NO: 12) p151–165 (SEQ ID NO: 16) and p321–335 (SEQ ID NO: 20) derived from Cry j 2, and 8) DRB1*1501 binds to antigen peptides p36–50 (SEQ ID NO: 13) and p236–250 (SEQ ID NO: 19) derived from Cry j 2.

A core sequence of antigen peptide p106–120 (SEQ ID NO: 3) derived from Cry j 1 is p109–117 (SEQ ID NO: 4).

Ikagawa et al. reported that Cry j 1 antigen peptide p335–346 (SEQ ID NO: 11) was presented by DRB3*0301 (Ikagawa, S. et al.: J. Allergy Clin. Immunol. 97: 53–64, 1996). Hori et al. reported that Cry j 1 antigen peptide p214–222 (SEQ ID NO: 24) was presented by DPA1*0202-DPB1*0501 (Hori et al.: Tissue Antigens, 47: 481–491, 1996).

It has been conventionally hypothesized that there is a bias in the use of HLA class II (at the locus level) molecules that is determined by the antigen. The above studies revealed that, in principle, all DR, DQ, and DP molecules are used as restriction molecules presenting antigen peptides derived from Cry j 1 or Cry j 2, without bias.

Major HLA class II molecules binding to the specific antigens in Cry j 1 include DPA1*0101-DPB1*0501 binding to p61–75 (SEQ ID NO: 2), DQA1*0102-DQB1*0602 binding to p146–160 (SEQ ID NO: 5), and DPA1*0101-DPB1*0501 binding to p211–225 (SEQ ID NO: 8). In Cry j 2 these include DRB1*0901 binding to p16–30 (SEQ ID NO: 12), DRB1*1501 binding to p36–50 (SEQ ID NO: 13), DPA1*0101-DPB1*0501 binding to p76–90 (SEQ ID NO: 15), DRB4*0101 binding to p186–200 (SEQ ID NO: 18), and DPA1*0202-DPB1*0501 binding to p336–350 (SEQ ID NO: 22). The other peptides can bind not only to the identified restriction molecules but also to other molecules, and are thus characterized as multibinder peptides.

In general, an antigen peptide binding to a specific HLA molecule contains a common HLA binding amino acid motif. HLA binding amino acid motifs are necessary for antigen peptides to bind to HLA molecules. HLA molecules do not have high selectivity for binding to antigen peptides though other peptide hormone receptors have high selectivity to their ligands. Therefore, HLA molecules can bind to various potential antigen peptides. In HLA class II molecules, a binding motif of an antigen peptide consists of 3 to 5 amino acid residues separately located with 1 to 2 amino acids interposed (Matsushita, S. et al.: J. Exp. Med. 180: 873–883, 1994; Rammensee, H. -G. et al.: Immunogenet. 41: 178–228, 1995). Using these known HLA class II binding motifs, antigen peptides which can bind to the exemplified HLA class II molecules can be further selected based on the primary structure of the cryptomeria pollen allergenic molecule. Therefore, antigen peptides of the present invention which bind to a specific HLA class II type possessed by a patient suffering from a cryptomeria pollen allergy are not limited to antigen peptides exemplified in the present invention, but include antigen peptides expected to bind to specific HLA class II types.

The above-described antigen peptides binding to specific HLA class II types can be used as a peptide-based immunotherapeutic agent for a patient having said HLA class II types. When the antigen peptide of the present invention is used as a peptide-based immunotherapeutic agent to treat an allergy patient, it can be combined with pharmaceutically acceptable diluents and carriers. The resulting composition can be administered by simple methods such as injection (subcutaneous or intradermally), instillation, rhinenchysis, oral administration, inhalation, percutaneous application, or trans-mocus. Dosage can be determined by usual methods by one skilled in the art.

To select a peptide-based immunotherapeutic agent suitable for each patient, the HLA class II type of the patient should be determined. The HLA class II type of a patient can be determined by using an antigen peptide specifically reacting with the HLA class II molecule as a reagent.

Specifically, HLA class II molecules of an allergic patient and a healthy subject can be typed as follows. Amino acid motifs of antigen peptides binding to each molecule vary depending on the HLA class II types due to their high polymorphism. HLA class II molecules of a patient and a healthy person can thus be typed by labeling antigen peptides having different binding motifs and detecting the specific binding to HLA class II molecules. Antigen peptides can be labeled by binding a known label, such as a radioisotope, an enzyme, a fluorescent label, or a luminescent label, to an amino acid residue (for example a tyrosine residue) other than the HLA anchor amino acid residues of the antigen peptides. Alternatively, biotinylated antigen peptides are detected with streptavidin (or avidin) bound to the above label. An allergic patient can be diagnosed by culturing peripheral blood lymphocytes of the subject in the presence of various antigen peptides derived from the allergen and monitoring T-cell response by, for example, adding [$^3$H]thymidine to the culture medium and measuring the amount of [$^3$H]thymidine uptake. Moreover, if T-cell response can be found in a subject (an allergic-response-positive patient), the type of the subject's HLA class II molecules restricting the antigen peptides that induced the T-cell response can be identified as the HLA class II type endowing susceptibility to said allergen in the subject.

The correlation between the patient's HLA class II type and the antigen peptides identified by this method can be used to study the role of each HLA class II type in the onset of allergy or to select antigen peptides to be used in a peptide-based immunotherapeutic agent for the allergic patient.

A peptide-based immunotherapeutic agent for a particular allergic patient whose HLA class II molecule type has been identified can be prepared by selecting an antigen peptide compatible with the HLA type of said patient, measuring the response to the peptide to proliferate peripheral blood lymphocytes derived from the patient, and comparing the level of the response of the peptide. For example, the haplotypes of HLA class I and class II of patient PB suffering from cryptomeria pollen allergy described in Example 6 are: A2/24-B39/55-Cw7/w3-DRB1*1501/0901-DRB4*0101-DRB5*0101, DQA1*0102/0301-DQB1*0602/0303, and DPA1*0101/0101-DPB1*0501/0201. When antigen peptides to be used for peptide-based immunotherapy for said patient are selected, the antigen peptides p211–225 (SEQ ID NO: 8) presented by DPA1*0101-DPB1*0501, p106–120 (SEQ ID NO: 3) presented by DBR5*0101, p191–205 (SEQ ID NO: 7) or p251–265 (SEQ ID NO: 9) presented by DQA1*0102-DQB1*0602 should be selected in Cry j 1; in Cry j 2, p76–90 (SEQ ID NO: 15) presented by DPA1*0101-DPB1*0501, p186–200 (SEQ ID NO: 18) presented by DRB4*0101, and p66–80 (SEQ ID NO: 14) presented by DRB5*0101 should be selected. Before peptide-based immunotherapy is effected using these antigen peptides, the response to these antigen peptides to proliferate peripheral blood lymphocytes derived from the patient should be measured to select the antigen peptides exhibiting a relatively high proliferation activity, which antigen is to be used for peptide-based immunotherapy.

In order to improve solubility, therapeutic or prophylactic effects, and stability of the effects, the antigen peptide of the present invention can be modified by substituting deleting, or adding amino acid residues other than the HLA anchors without spoiling their function. A certain amino acid can be suitably substituted with Ala, Ser, Glu, or methyl amino acids, but substituent amino acids are not limited thereto. Cys residue forms a dimer through a disulfide bond and functions as a multi-binder. Therefore, immunization with a peptide containing a Cys residue may cause recognition of sites which are not originally involved in antigenicity and thereby create new epitopes. In this case, a Cys residue can be substituted with Ala, Ser, Thr, Leu, or Glu. It may also be substituted by a D amino acid or a non-natural amino acid. A vector capable of expression of a polypeptide with a peptide composed of a histidine polymer (for example, a histidine hexamer) at its N- or C-terminus has been developed. The expression product can be purified by affinity chromatography using a nickel chelating column even in the presence of a denaturant. Such an embodiment is also included in the present invention.

The antigen peptide of the present invention can be derived from one allergen molecule or two or more different molecules. All protein allergens can be used in the present invention, including pollens of herbage such as ragweed, dactylis, and perennial ryegrass; pollens of arbors such as cryptomeria, chamaecyparis, and mountain cedar; mites; animals; fungi; insects; and foods.

BRIEF DESCRIPTION OF THE DRAWINGS

FIG. 3 shows the epitope sites recognized by T-cell clones which recognize Cry j 1, the molecules restricting said clones, the production of lymphokines by said clones, and Th types of said clones. In the figure, Th2 stands for IL-4/IFN-γ>10, Th1 for IFN-γ/IL-4>10, and Th0 for a level intermediate therebetween.

FIG. 4 shows the epitope sites recognized by T-cell clones which recognize Cry j 1, the restriction molecules of said clones, the production of lymphokines by said clones, and Th types of said clones. In the figure, Th2 stands for IL-4/IFN-γ>10, Th1 for IFN-γ/IL-4>10, Th0 for a level intermediate therebetween, and Thp for no lymphokine production.

BEST MODE FOR IMPLEMENTING THE INVENTION

Figure 1A:
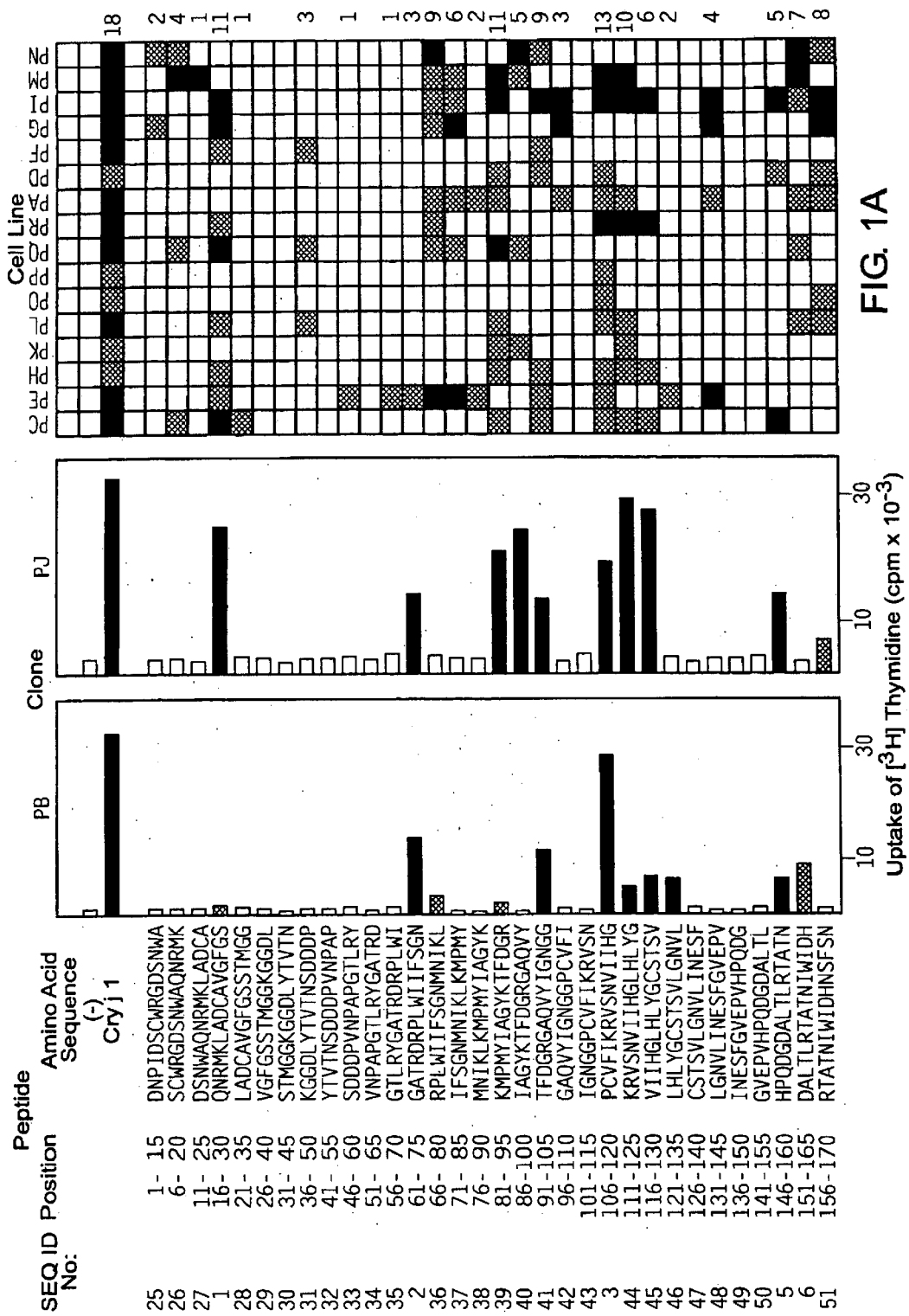
FIG. 1 shows the overlapping peptides of Cry j 1 containing epitopes recognized by patient's T-cells. In the figure, □ indicates 2≦SI<5 and ■ 5≦SI. T-cell clones were prepared from PB and PJ.

The present invention is illustrated with reference to the following examples, but is not construed to be limited thereto.

Example 1
Purification of Cryptomeria Pollen Antigen
Cry j 1 was purified by the method of Yasueda et al. (Yasueda, H. et al., J. Allergy Clin. Immunol. (1983) 71: 77–86). Cry j 2 was purified by inserting the Cry j 2 gene (unexamined published Japanese patent application (JP-A) No. Hei 8-47392) into expression vector pQE9 (Qiagen GmbH, Germany), transforming E. coli with the vector to express the gene, and purifying the gene expression product by affinity column chromatography using $Ni^{2+}$-NTA-agarose (Quiagen, Inc. USA) (Komiyama, N. et al., Biochm. Biophys. Res. Commun. (1994) 201: 1021–1028).

Example 2
Synthesis of Overlapping Peptides
Based on the primary structures of Cry j 1 (WO94/01560) and Cry j 2 (JP-A No. Hei 8-47392), 69 kinds of overlapping peptides for Cry j 1 (FIG. 1) and 74 kinds for Cry j 2 (FIG. 2) were synthesized with a peptide synthesizer (Shimadzu, PSSM-8 model). These overlapping peptides cover all the primary structures of Cry j 1 or Cry j 2 and consist of 15 amino acid residues in which the overlapping portion has 10 residues. The peptides were dissolved in PBS containing 8M urea to 2 mM. When the peptides were added to the culture system for assaying T-cell proliferation response, the peptides were diluted 500-fold to eliminate the effect of urea.

Example 3
Establishing Antigen Presenting Cells
Peripheral blood lymphocytes were isolated from peripheral blood from a patient suffering from cryptomeria pollen allergy by the Ficoll-paque (Pharmacia) specific gravity centrifugation method. B95-8 cell (derived from a marmoset, ATCC CRL1612) culture supernatant with Esptein-Barr (EB) virus was added to $1 \times 10^6$ peripheral blood lymphocytes to infect B cells in peripheral blood lymphocytes with EB virus. Infected B-cells were cultured in RPMI-1640 medium with 200 ng/ml of cyclosporin A and 20% fetal calf serum (FCS) for about 20 days to establish transformant B cell lines.

Example 4
Establishing T-cell Lines and T-cell Clones
$4 \times 10^6$ peripheral blood lymphocytes were suspended in 2 ml of RPMI-1640 medium supplemented with 20% human serum, and cultured for 8 days in the presence of 50 μg/ml of Cry j 1 or 2 to 10 μg/ml of Cry j 2 to activate T cells recognizing Cry j 1 or Cry j 2.

When activated T cells appeared, T-cell lines specifically recognizing Cry j 1 or Cry j 2 were established by replacing the medium with RPMI-1640 medium with 200 U/ml of IL-2 (Boehringer-Mannheim) and 15% human serum and culturing the cells for an additional 14 days.

T-cell clones specifically recognizing Cry j 1 or Cry j 2 were established as follows. When the activated T cells appeared, T cells were spread in a 10-cm culture dish and selected one-by-one using a micropipet. Separately, the same nonactivated cells transfected with EB virus were treated with mitomycin C (Kyowa Hakko Kogyo) and inoculated into each well of a 96-well microculture plate at $1 \times 10^5$ cells/well. The above activated T cells were transferred to the 96-well plate, one cell per well. An additional 50 μg/ml of Cry j 1 or 2 to 10 μg/ml of Cry j 2 was added to each well and cultured for 7 days for challenge. The challenge at an interval of 7 days was repeated two or three times to establish T-cell clones.

Example 5
Identifying Cry j 1 and Cry j 2 T-cell Epitopes
Peripheral blood lymphocytes derived from 18 patients suffering from cryptomeria pollen allergy were challenged by Cry j 1 or Cry j 2 to establish T-cell lines specifically recognizing Cry j 1 or Cry j 2 for each individual patient. $5 \times 10^4$ cells of self-derived B-cell line treated with mitomycin C, 2 μM of overlapping peptides, and $2 \times 10^4$ cells of the T-cell line were cultured in RPMI-1640 medium supplemented with 0.2 ml of 15% serum in a 96-well microplate for two days. 0.5 μCi of [$^3$H]thymidine was added, and the culture medium was cultured for an additional 18 hours. The cells were collected in a glass filter with a cell harvester, and uptake of [$^3$H]thymidine was measured with a liquid scintillation counter. T cells capable of recognizing antigenic information of Cry j 1 or Cry j 2 as well as HLA class II molecules proliferated and incorporated [$^3$H]thymidine. Cells exhibiting a Stimulation Index of 2 or higher were considered to have recognized the relevant added antigen peptides.

Figure 1B:
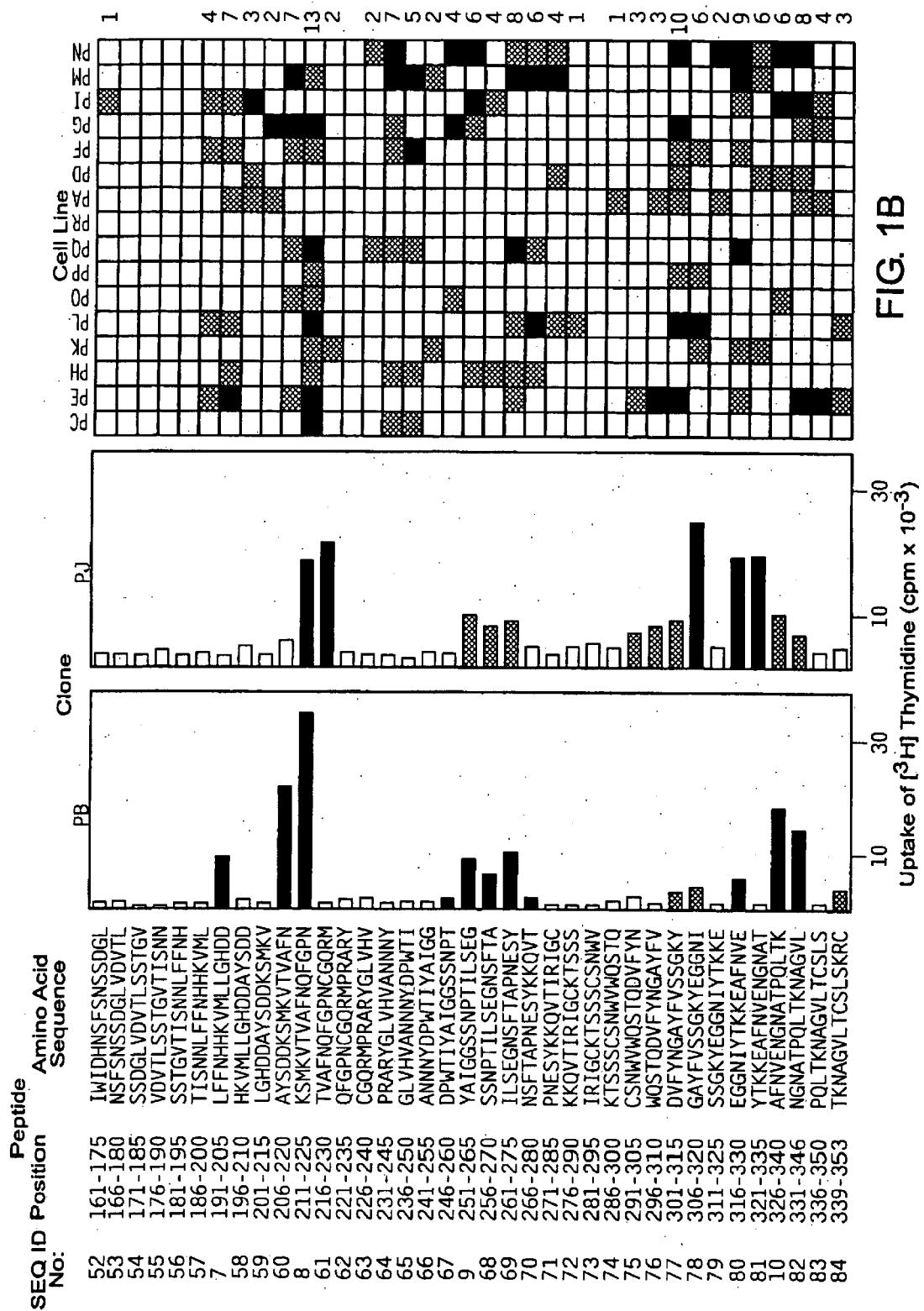
Figure 2A:
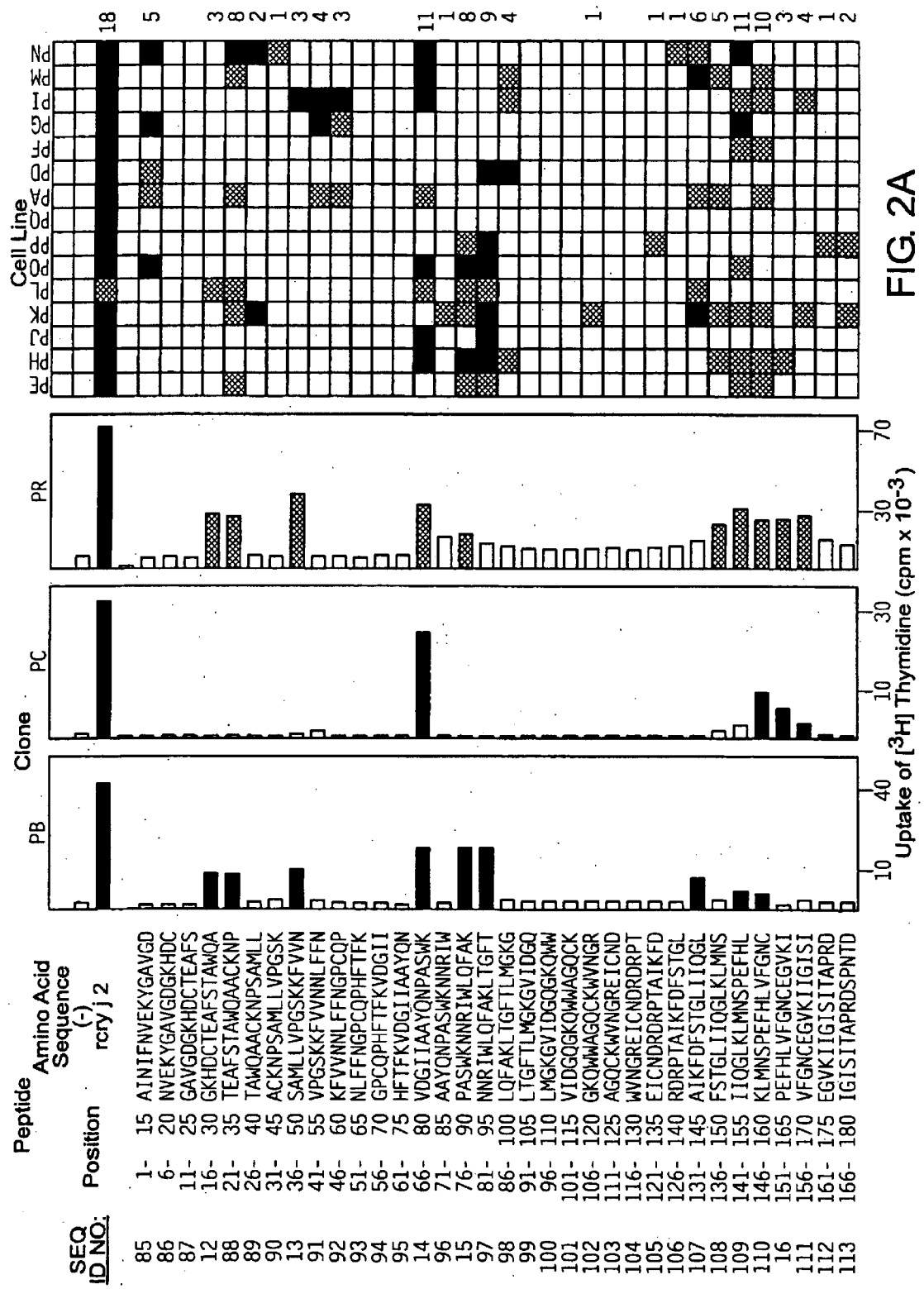
FIG. 2 shows the overlapping peptides of Cry j 2 containing epitopes recognized by patient's T-cells. In the figure, □ indicates 2≦SI<5 and ■ 5≦SI. T-cell clones were prepared from PB, PC and PR.
Figure 2B:
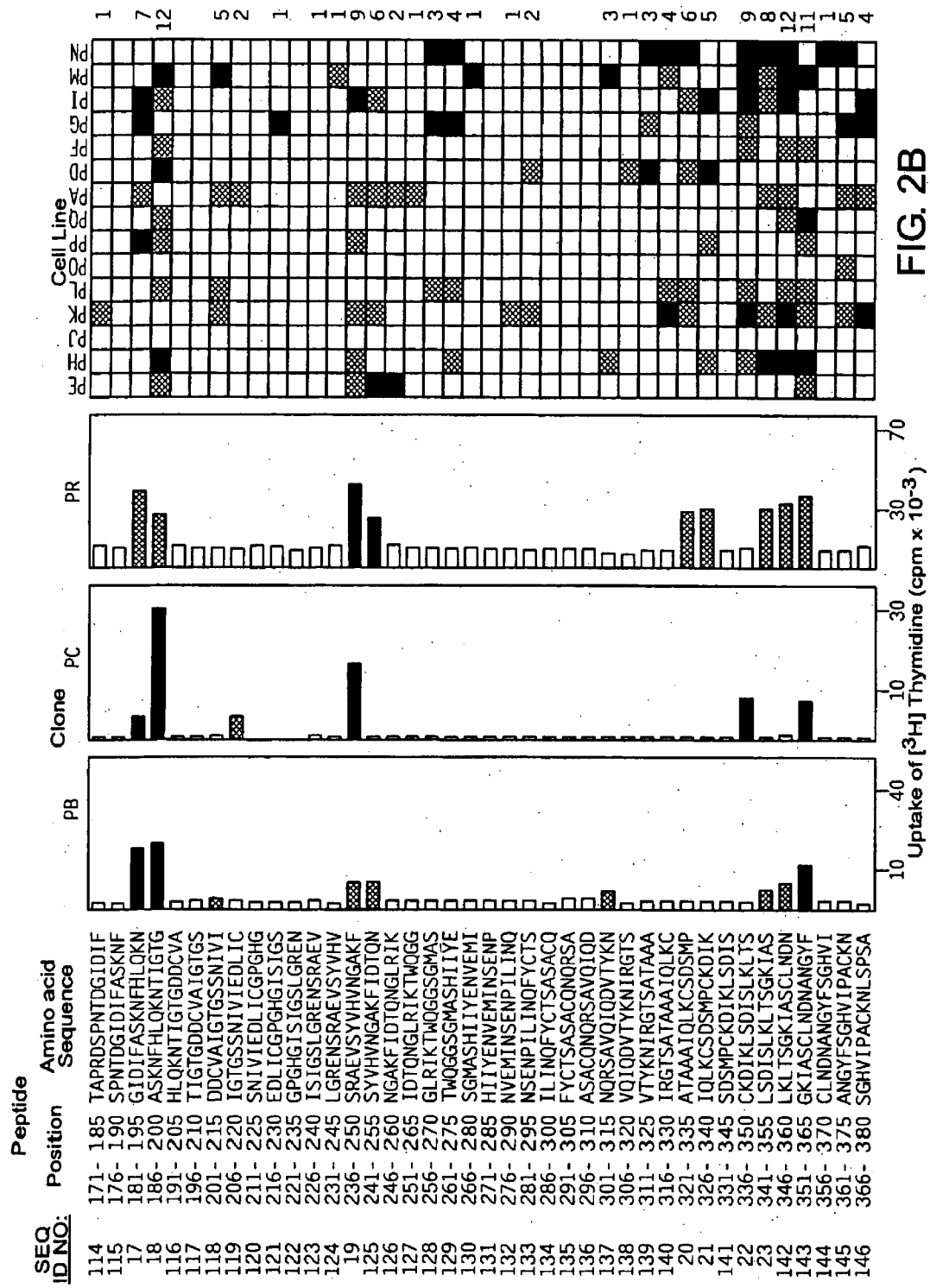

The number of T-cell epitope sites of Cry j 1 recognized by each patient was 9.8±3.0 on average and ranged from 4≦15 epitopes. Using T-cell lines recognizing Cry j 2, the number of T-cell epitope sites recognized by each patient was 8.7±3.3 on average and ranged from 2≦13 epitopes. Since Cry j 1 is composed of 353 amino acids (International patent application published in Japan No. Hei 8-502163) and Cry j 2 is composed of 379 amino acids (JP-A No. Hei 8-47392), the above results mean that about 2.3 to 2.8 T-cell epitope sites exist per 100 amino acid residues. Each patient has different HLA class II types and therefore recognizes different T-cell epitopes depending on the HLA class II types. An epitope map was prepared by marking T-cell epitope sites on the Cry j 1 or Cry j 2 molecule T-cell epitope sites recognized by each patient on the Cry j 1 or Cry j 2 molecule. The results are shown in FIGS. 1 and 2.

Example 6
Identification of T-cell Epitopes Recognizing T Cell Clones

Among 18 patients suffering from a cryptomeria pollen allergy, 2 patients recognizing antigen peptides p211–225 (SEQ ID NO:8) and p106–120 (SEQ ID NO:3) of Cry j 1 [patient B (hereinafter referred to as PB), and patient J (hereinafter referred to as PJ)], 3 patients recognizing antigen peptides p66–80 (SEQ ID NO:14), p186–200 (SEQ ID NO:18), p236–250 (SEQ ID NO:19), and p341–355 (SEQ ID NO:23) of Cry j 2 [PB, patient C (hereinafter referred to as PC), and patient R (hereinafter referred to as PR)] were selected. T-cell clones recognizing Cry j 1 or Cry j 2 were established by stimulating peripheral blood lymphocytes of these cryptomeria pollen allergy patients by Cry j 1 or Cry j 2. HLA class I and II types of the four patients are as follows: PB: A2/24-B39/55-Cw7/w3-DRB1*1501/0901-DRB4*0101-DRB5*0101, DQA1*0102/0301-DQB1*0602/0303-DPA1*0101/0101-DPB1*0501/0201; PJ: A24/--B61/51-Cw3/--DRB1*1501/0802-DRB5*0101, DQA1*0102/0401-DQB1*0602/0402-DPA1*-/--DPB1*0501/0402; PC: A-2/2-B54/51-Cw1/-, DRB1*0405/1501-DRB4*0101-DRB5*0101-DQA1*0301/0102-DQB1*0401/0602-DPA1*0202/0202-DPB1*0201/0501; PR: A-11/--B60/35-Cw7/w3-DRB1*0901/1501-DRB4*0101-DRB5*0101-DQA1*0301/0102-DQB1*0303/0602-DPA1*01/0202-DPB1*0201/0201.

35 and 14 types of T-cell clones specifically recognizing Cry j 1 were established from the peripheral blood lymphocytes derived from PB and from PJ, respectively. Similarly, 31, 10, and 17 types of T-cell clones specifically recognizing Cry j 2 were established from the peripheral blood lymphocytes derived from PB, PC, and PR respectively. All of these T-cell clones were CD3$^+$, CD4$^+$, CD8$^-$, TCR-αβ$^+$, TCR-γδ$^-$, therefore, the restriction molecules were HLA class II molecules. Self-derived 5×10$^4$ B-cell lines treated with mitomycin C, 2 μM of the overlapping peptides, and 2×10$^4$ T-cell clones were cultured in RPMI-1640 medium supplemented with 0.2 ml of 15% serum on a 96-well microplate for 2 days. After 0.5 μCi of [$^3$H]thymidine was added, the cells were further cultured for 18 hours. The cells were collected in a glass filter by a cell harvester and uptake of [$^3$H] thymidine was measured using a liquid scintillation counter. T-cell epitopes recognized by each T-cell clone were identified by the above manipulation. Sixty-nine percent (34/49) of T-cell clones recognizing Cry j 1 proliferated in response to stimulation by the peptide containing T-cell epitopes and the antigen peptides were identified. Similarly, antigen peptides were identified among 69% (40/58) of T cell clones recognizing Cry j 2. T-cell clones specifically recognizing Cry j 1 recognized peptides p16–30 (SEQ ID NO:1), p61–75 (SEQ ID NO:2), p91–105 (SEQ ID NO:41), p106–120 (SEQ ID NO:3), p146–160 (SEQ ID NO:5), p151–165 (SEQ ID NO:6), p191–205 (SEQ ID NO:7), p211–225 (SEQ ID NO:8), p251–265 (SEQ ID NO:9), p326–340 (SEQ ID NO:10), and p331–346 (SEQ ID NO:82). T-cell clones specifically recognizing Cry j 2 recognized peptides p16–30 (SEQ ID NO:12), p21–35 (SEQ ID NO:88), p36–50 (SEQ ID NO:13), p66–80 (SEQ ID NO:14), p76–90 (SEQ ID NO:15), p81–95 (SEQ ID NO:97), p151–165 (SEQ ID NO:16), p181–195 (SEQ ID NO:17), p186–200 (SEQ ID NO:18), p236–250 (SEQ ID NO:19), p321–335 (SEQ ID NO:20), p326–340 (SEQ ID NO: 21), p336–350 (SEQ ID NO:22), p341–355 (SEQ ID NO:23), and p346–360 (SEQ ID NO:142). The results are summarized in FIGS. 1 and 2 (the histograms in the center).

Example 7
Identification of HLA Class II Restriction Molecule Loci

HLA class II restriction molecules were identified at the locus level by adding monoclonal antibodies specifically reacting with HLA-class II-DR, HLA-class II-DQ, or HLA-class II-DP to the proliferation response system of T-cell clones established in Example 4 so as to inhibit T cell proliferation response.

Self-derived 2×10$^4$ B-cell lines treated with mitomycin C, 2 μM of the overlapping peptides, 3 μg/ml of anti-DR, DQ, or DP monoclonal antibody (Becton/Dickinson), and 2×10$^4$ T-cell clones were cultured in RPMI-1640 medium with 0.2 ml of 15% serum for 2 days. After 0.5 μCi of [$^3$H]thymidine was added, culturing was performed for further 18 hours. The cells were collected in a glass filter using a cell harvester, and uptake of [$^3$H]thymidine was measured using a liquid scintillation counter.

Example 8
Identification of Restriction Molecules of Each Type of HLA Class II Molecules Restriction molecules of each HLA class II type of T-cell clones whose restriction molecules were identified at the locus level can be identified by using, as antigen-presenting cells, mouse L-cells transformed with the DR gene and B-cell lines that are homozygous at the DQ or DP loci.

5×10$^4$ of the above mouse L-cells or haplotype matching B-cell lines, treated with mitomycin C, 2 μM of overlapping peptides, 3 μg/ml of anti-DR, DQ, or DP monoclonal antibody (Becton/Dickinson), and 2×10$^4$ T-cell clones were cultured in RPMI-1640 medium with 0.2 ml of 15% serum for 2 days. After 0.5 μCi of [$^3$H]thymidine was added, culturing was further continued for 18 hours. The cells were collected in a glass filter using a cell harvester, and uptake of [$^3$H]thymidine was measured using a liquid scintillation counter. Restriction cells can be identified when proliferation response of T-cell clones are observed. The results of the analysis are shown in FIGS. 3 and 4.

Example 9
Identification of Th Types for T Cell Clones

Th2 cells are presumably involved in onset of allergy. It has not been revealed yet as to whether differentiation of T cells to Th1 or Th2 cells in response to antigenic stimulation is controlled by the specific epitope peptides or the HLA-class II locus. If Th2 cells are primarily induced after stimulation by the peptides for selecting antigen peptides, cryptomeria pollen allergy would worsen due to administration of the peptides. To examine the above hypothesis, Th types for the T-cell clones prepared in Example 4 were determined by stimulating the clones by the epitope peptides recognized by the T cells, and measuring production of IL-2, IL-4, and IF-Nγ.

Specifically, self-derived 1×10⁵ B-cell lines treated with mitomycin C, 2 μM of epitope peptides, and 5×10⁵ T-cell clones were cultured in RPMI-1640 medium with 1 ml of 10% human serum for 24 hours, then the supernatant was obtained by centrifugation. IL-2, IL-4, and IFN γ in the supernatant were determined using the commercially available ELISA kit [IL-2 (R&D), IL-4 (Medojenics), and IFNγ (Otsuka Assay Laboratory)].

FIGS. 3 and 4 show the production of IL-2, IL-4, and IFN-γ and Th types of each clone. The number of T-cell clones recognizing Cry j 1 are 12 Th2 clones, 1 Th1 clone, and 16 Th0 clones. Thus the number of Th2 was larger than that of Th1. In contrast, the number of T-cell clones recognizing Cry j 2 are 10 Th2 clones, 8 Th1 clones, and 8 Th0 clones. Thus the number of Th1 was almost the same as that of Th2. In comparing T cell epitopes recognized by each T cell clone, the restriction molecules, and Th types, it was found that each T-cell clone was different with respect to Th type. For several T cell clones recognizing the same epitopes and same antigen-presenting molecules, both Th2 and Th1 cells were identified. These findings indicate that differentiation of T cells to Th2, Th1, or Th0 cells after stimulation by Cry j 1 or Cry j 2 is not determined by the combination of specific T-cell epitopes or specific restriction molecules. In other words, any peptide containing T-cell epitope sites can stimulate T cells and can be selected as peptides for use as a peptide-based immunotherapeutic agent.

Example 10
Identification of T-cell Epitopes in CB6F1 Mouse

Eight-week-old male CB6F1 mice were immunized with 10 μg of recombinant Cry j 2 (rCry j 2) together with an adjuvant (Imject Alum, PIERCE) three times every two weeks (ip). One week after the last immunization, splenocytes were prepared from three mice and combined. 0.115 μM each of 74 overlapping peptides consisting of 15 amino acid residues was cultured separately with 5×10⁶ splenocytes in 0.2 ml of RPMI-1640 medium (10% FCS, 2 mM L-glutamine, 50 U/ml penicillin, and 50 μg/ml streptomycin) in each well of a 96-well plate (Falcon). As the control, the responses to PBS, 50 μg/ml of Cry j 1, 0.3 μg/ml of rCry j 2 were assessed. Each reagent was inoculated in three wells and cells were cultured at 37° C. in 5% $CO_2$ for three days. Pulse labeling was performed with 0.5 μCi/well of [³H]thymidine for the last 6 hours and the cells were collected in a glass filter using a cell harvester (Inoteck, Bertold Japan). After the cells were dried, uptake of [³H]thymidine into the cells was measured with a liquid scintillation counter (TRI-CARB 4530, Packard Japan).

CB6F1 mice immunized with rCry j 2 showed a strong response to rCry j 2 antigen, but did not respond to another cryptomeria pollen major allergen Cry j 1, indicating that this system was antigen-specific reaction. Of the 74 overlapping peptides tested, splenocytes from CB6F1 mice immunized with rCry j 2 showed remarkable responses to p66–80 (SEQ ID NO: 14) and p236–250 (SEQ ID NO: 19). These results indicated that p66–80 and p236–250 peptides are presented as major epitopes of Cry j 2 in CB6F1 mice. In humans, p66–80 (SEQ ID NO: 14) and p236–250 (SEQ ID NO: 19) are also major T cell epitope peptides. Thus, CB6F1 mice can be a useful model animal to evaluate the effectiveness of peptide compositions to be used in peptide-based immunotherapy for cryptomeria pollen allergy.

Example 11
In Vivo Immunoreaction of Antigen Peptide p66–80 (SEQ ID NO: 14)

Three mg of p66–80 peptide (SEQ ID NO: 14) dissolved in physiological saline was subcutaneously administered to an eight-week-old male mouse twice at an interval of 5 days. Similarly, the same volume (100 μl) of physiological saline was administered to mice of the control group. Both the peptide-administered group and a control group had eight mice. Five days after the second peptide administration, 50 μg of rCry j 2 mixed with an adjuvant, Imject Alum, was subcutaneously administered to all mice for immunization. One week after the immunization, splenocytes were prepared from each mouse, 5×10⁶ splenocytes were cultured together with 3 μg/ml of rCry j 2 in 0.2 ml of RPMI medium (10% FCS, 2 mM L-glutamine, 50 U/ml penicillin, and 50 μg/ml streptomycin) in each well of a 96-well plate (Falcon). As the control, the cells were cultured in the same medium containing no rCry j 2. Uptake of [³H]thymidine was measured as described in Example 10.

Figure 5:
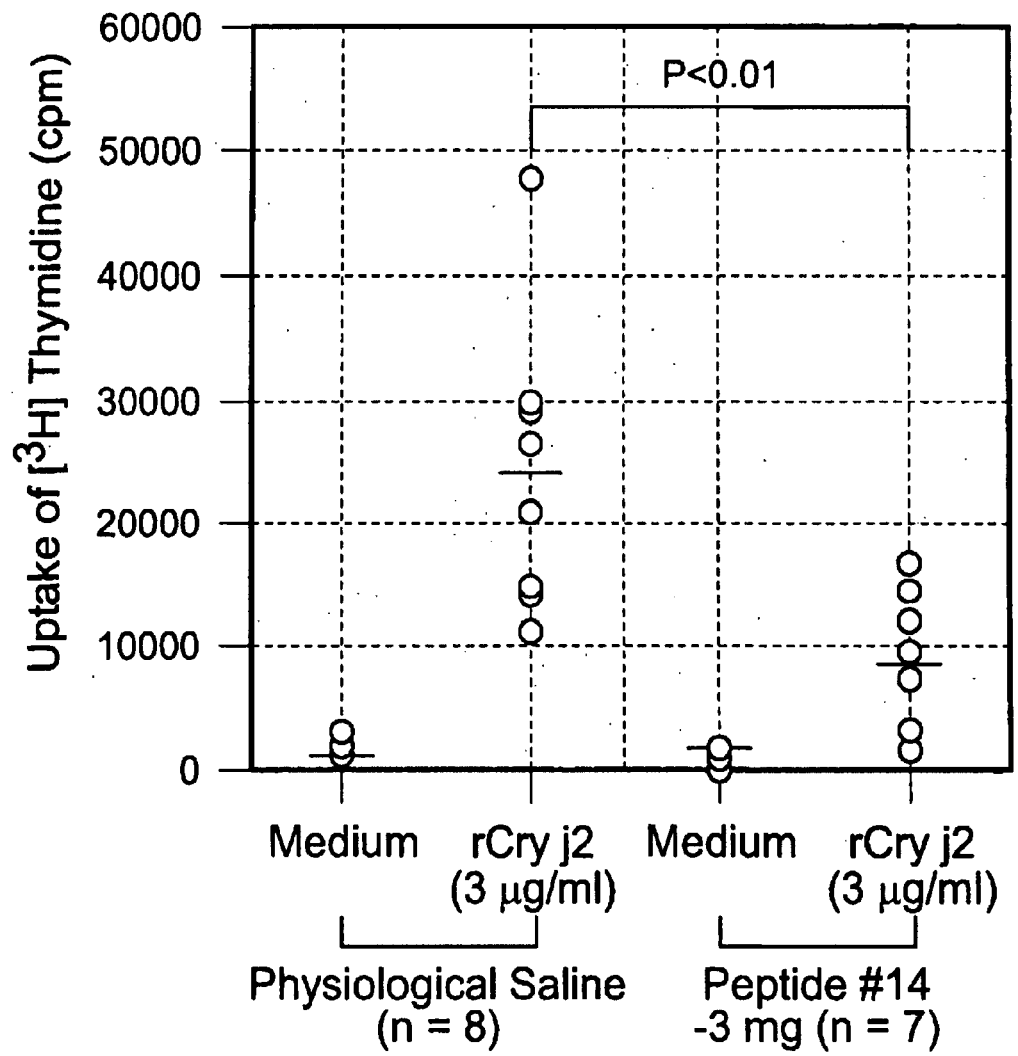
FIG. 5 shows the immune responses of CB6F1 mice to Cry j 2 when the antigen peptide p66–80 of Cry j 2 was administered to the mice.

When p66–80 (SEQ ID NO: 14) was subcutaneously administered to CB6F1 mice before antigen stimulation by rCry j 2, immune response of the T cells was significantly inhibited compared to the physiological saline-administered group (p<0.01) (FIG. 5). This result indicated that in the mouse model p66–80 (SEQ ID NO: 14) system showed a preventive effect in peptide-based immunotherapy for treating cryptomeria pollen allergy.

Example 12
In Vivo Immune Response to Antigen Peptide p236–250 (Peptide No. 48) (SEQ ID NO: 19)

Three mg of p236–250 peptide (SEQ ID NO: 19) dissolved in physiological saline was subcutaneously administered to a six-week-old male mouse twice at an interval of 5 days. As a control, the same volume (200 μl) of physiological saline was administered to mice in the same manner as above. Both the peptide-administered group and the control group had eight mice. Five days after the second peptide administration, 50 μg of rCry j 2 mixed with adjuvant Imject Alum was subcutaneously administered to all mice. One week after the immunization, splenocytes were prepared from each mouse. 5×10⁶ splenocytes were cultured together with 3 μg/ml of rCry j2 in 0.2 ml of RPMI medium (10% FCS, 2 mM L-glutamine, 50 U/ml penicillin, and 50 μg/ml streptomycin in each well of a 96-well plate (Falcon). As a control, the cells were cultured in the same medium containing no rCry j 2. Uptake of [³H]thymidine was measured as described in Example 10.

Figure 6:
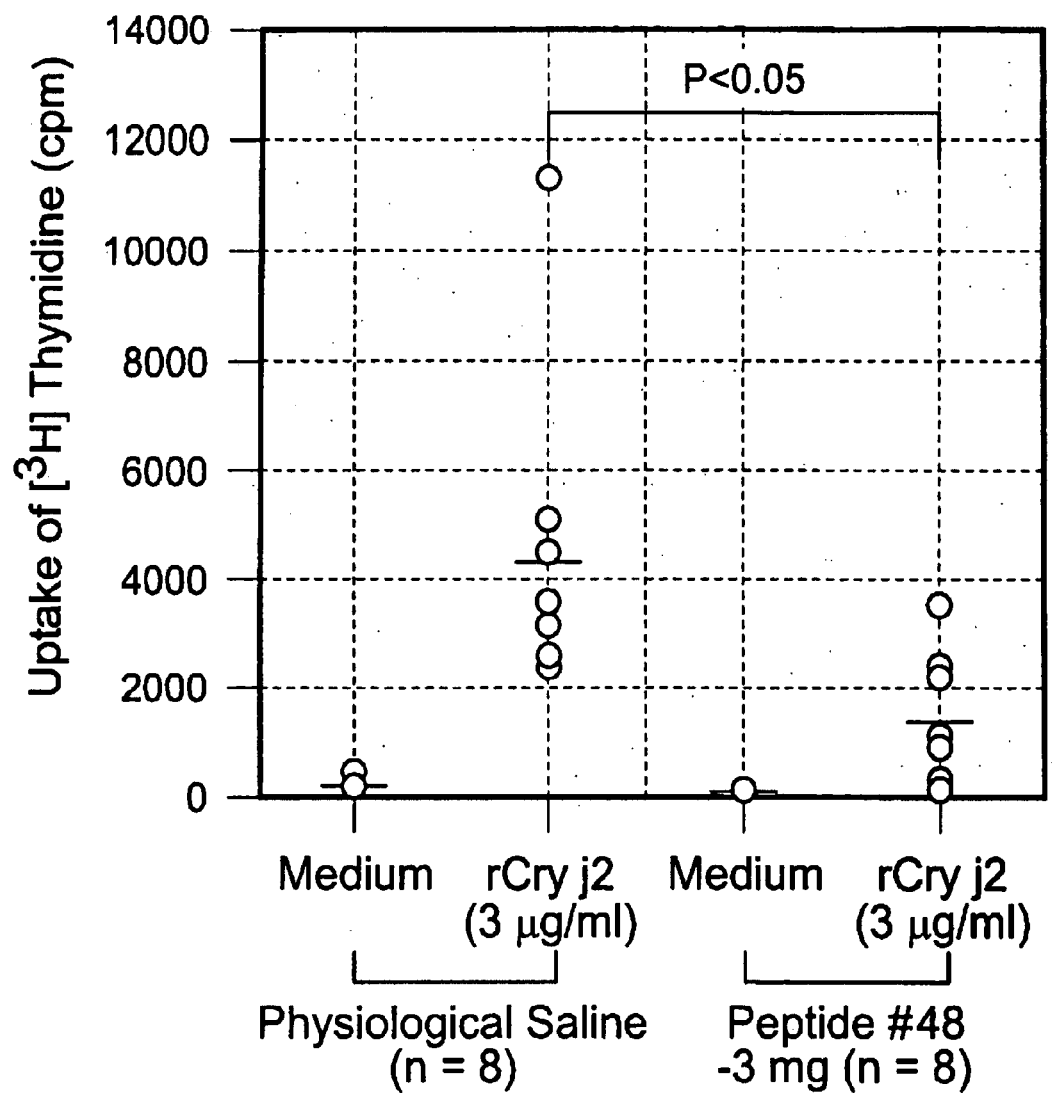
FIG. 6 shows the immune responses of CB6F1 mice to Cry j 2 when the antigen peptide p186–200 of Cry j 2 was administered to the mice.

When p236–250 (SEQ ID NO: 19) was subcutaneously administered to CB6F1 mice before antigenic stimulation by rCry j 2, immune response of the T cells was significantly inhibited compared to the physiological saline-administered group (p<0.05) (FIG. 6). This result indicated that in the mouse model system p236–250 (SEQ ID NO: 19) showed a preventive effect in peptide-based immunotherapy for treating cryptomeria pollen allergy.

The above results revealed that the conventional hyposensitization in humans using a cryptomeria pollen extract was based on the mechanism mediated by T-cell epitopes.

Industrial Applicability

According to the present invention, an antigen peptide that binds to a haplotype of HLA class II molecules of an allergic patient can be used as a peptide-based immunotherapeutic agent for that patient. The present invention enables the optimal peptide-based immunotherapy for individual patients. Thus the effectiveness of peptide-based immunotherapy is expected to be remarkably improved. Furthermore, the present invention provides a peptide-based immunotherapeutic agent effective for a patient who cannot be treated by peptide-based immunotherapy using major antigen peptides recognized in a specific patient population.

In addition, typing of HLA class II molecules of an allergy patient can be simply and easily performed using an antigen peptide of the present invention.

What is claimed is:

1. A method for treating Japanese cedar pollen allergy in a subject in need thereof, the method comprising:
   (a) identifying an HLA class II molecule expressed by the subject;
   (b) selecting an antigenic peptide derived from Japanese cedar pollen allergen Cry j 1 or Cry j 2, wherein the antigenic peptide binds to HLA class II molecule and wherein:
      (1) when the HLA class II molecule identified in step (a) is DQA1*0102-DQB1*0602, the antigenic peptide is selected from the group consisting of SEQ ID NO: 1, 5, 7, 9, 10, 21, 23, and 142;
      (2) when the HLA class II molecule identified in step (a) is DPA1*0101-DPB1*0501, the antigenic peptide is selected from the group consisting of SEQ ID NO: 2, 8, and 15;
      (3) when the HLA class II molecule identified in step (a) is DPA1*0101-DPB1*0201, the antigenic peptide is SEQ ID NO: 17;
      (4) when the HLA class II molecule identified in step (a) is DPA1*0202-DPB1*0501, the antigenic peptide is SEQ ID NO: 22;
      (5) when the HLA class II molecule identified in step (a) is DRB5*0101, the antigenic peptide is selected from the group consisting of SEQ ID NO: 3, 4, 14, and 19;
      (6) when the HLA class II molecule identified in step (a) is DRB1*0901, the antigenic peptide is selected from the group consisting of SEQ ID NO: 6, 7, 12, 16, and 20;
      (7) when the HLA class II molecule identified in step (a) is DRB4*0101, the antigenic peptide is selected from the group consisting of SEQ ID NO: 7, 12, and 18; and
      (8) when the HLA class II molecule identified in step (a) is DRB1*0501, the antigenic peptide is selected from the group consisting of SEQ ID NO: 13 and 19; and
   (c) administering the selected antigenic peptide to the subject.

2. A customized pharmaceutical composition for treating a subject suffering from a Japanese cedar pollen allergy, the composition comprising:
   (a) an effective amount of an antigenic peptide derived from Japanese cedar pollen allergen Cry j 1 or Cry j 2, wherein the antigenic peptide binds to an HLA class II molecule expressed by the subject and wherein:
      (1) when the subject expresses the HLA class II molecule DQA1*0102-DQB1*0602, the antigenic peptide is selected from the group consisting of SEQ ID NO: 1, 5, 7, 9, 10, 21, 23, and 142;
      (2) when the subject expresses the HLA class II molecule DPA1*0101-DPB1*0501, the antigenic peptide is selected from the group consisting of SEQ ID NO: 2, 8, and 15;
      (3) when the subject expresses the HLA class II molecule DPA1*0101-DPB1*0201, the antigenic peptide is SEQ ID NO: 17;
      (4) when the subject expresses the HLA class II molecule DPA1*0202-DPB1*0501, the antigenic peptide is SEQ ID NO: 22;
      (5) when the subject expresses the HLA class II molecule DRB5*0101, the antigenic peptide is selected from the group consisting of SEQ ID NO: 3, 4, 14, and 19;
      (6) when subject expresses the HLA class II molecule DRB1*0901, the antigenic peptide is selected from the group consisting of SEQ ID NO: 6, 7, 12, 16, and 20;
      (7) when the subject expresses the HLA class II molecule DRB4*0101, the antigenic peptide is selected from the group consisting of SEQ ID NO: 7, 12, and 18; and
      (8) when the subject expresses the HLA class II molecule DRB1*0501, the antigenic peptide is selected from the group consisting of SEQ ID NO: 13 and 19; and
   (b) a pharmaceutically acceptable diluent or carrier.

* * * * *

UNITED STATES PATENT AND TRADEMARK OFFICE
CERTIFICATE OF CORRECTION

PATENT NO.         : 7,025,964 B1
APPLICATION NO.    : 09/308027
DATED              : April 11, 2006
INVENTOR(S)        : Akinori Kume et al.

It is certified that error appears in the above-identified patent and that said Letters Patent is hereby corrected as shown below:

On the Title Page, Item 56 References Cited Section - OTHER PUBLICATIONS, line 4: "Janpanese" should be --Japanese--.

On the Title Page, Item 57
In the Abstract, lines 1-3: "A peptide-based inmunotherapeutic agent effective for every allergy patient is provided. A reagent for typing HLA class II molecules of the patient to be used in selecting a peptide-based immunotherapeutic agent effective for every allergy patient is also provided."

should read as follows:

--Peptide-based immunotherapeutic agents effective for each individual allergy patient are provided. Reagents for typing HLA class II molecules of patients to be used in selecting peptide-based immunotherapeutic agents effective for each individual allergy patient are also provided.--.

Col 5, second paragraph, line 16, "challenge" should be --challenged--.

Col. 5, line 6, "to" should be --of--.

Col. 5, line 7, "allergy" should be--allergy.--.

Col. 5, line 7, "caused by antigen peptides presented by HLA-DPB1*0501. HLA-DPB1*0501 is frequently present in patients suffering from Cryptomeria pollen allergy induced by Cry j 1 and Cry j 2, and antigen peptides presented by different HLA class II molecules (DR.DQ or DP) (Japanese Patent Application No. Hei 8-70702)."

should read as follows:

--These multiple-epitope peptides comprise antigen peptides presented by different HLA class II molecules (DR, DQ or DP),and antigen peptides that are derived from both Cry j 1 and Cry j 2 and which are presented by HLA-DPB1*0501 (Japanese Patent Application No. Hei 8-80702). HLA-DPB1*0501 exists at a high frequency in patients suffering from cryptomeria pollen allergy.--

Col. 6, line 4, after "provided" please add --, for example,--.

Col. 6, line 5, "multiple" should be --multi--.

UNITED STATES PATENT AND TRADEMARK OFFICE
CERTIFICATE OF CORRECTION

PATENT NO. : 7,025,964 B1
APPLICATION NO. : 09/308027
DATED : April 11, 2006
INVENTOR(S) : Akinori Kume et al.

It is certified that error appears in the above-identified patent and that said Letters Patent is hereby corrected as shown below:

Col. 7, line 1, "there is a bias in the use of HLA class II (at the locus level) molecules that is determined by the antigen."

should read as follows:

--, depending on the antigen type, there is a bias towards restriction molecules at the HLA class II locus level, and that this defines immune reactions.--.

Col. 8, line 11, "Moreover, if T-cell response can be found in a subject (an allergic-response-positive patient), the type of the subject's HLA class II molecules restricting the antigen peptides that induced the T-cell response can be identified as the HLA class II type endowing susceptibility to said allergen in the subject."

should read as follows:

--For subjects showing a T cell response (allergy response-positive patients), the type of HLA class II restriction molecule for the antigen peptide that induces the T cell response can be identified as the subjects' HLA class II type.--.

Col. 8, line 65, "expression of a polypeptide with a peptide composed of"
should read as follows: --expressing, as a polypeptide, a peptide with--.

Col. 9, line 14, "shows the overlapping peptides of Cry j 1 containing epitopes recognized by patient's T-cells"

should read as follows: --shows Cry j 1 overlapping peptide sequences and the patients' T-cell epitope sites.--

Col. 9, line 18, "shows the overlapping peptides of Cry j 2 containing epitopes recognized by patient's T-cells"

should read as follows: --shows Cry j 2 overlapping peptides and the patients' T-cell epitope sites.--.

Col. 9, line 39, "shows the immune responses of CB6F1 mouse to Cry j 2 when the antigen peptide p186-200 of Cry j 2 was administered to the mouse."

should read as follows; --shows the immune response of CB6FI mice to Cry j 2 when the antigen peptide p236-250 of Cry j 2 was administered to the mice..--.

UNITED STATES PATENT AND TRADEMARK OFFICE
CERTIFICATE OF CORRECTION

PATENT NO. : 7,025,964 B1
APPLICATION NO. : 09/308027
DATED : April 11, 2006
INVENTOR(S) : Akinori Kume et al.

It is certified that error appears in the above-identified patent and that said Letters Patent is hereby corrected as shown below:

Col. 11, line 1, "The number of T-cell epitope sites of Cry j 1 recognized by each patient was 9.8 ± 3.0 on average and ranged from 4 ≤ 15 epitopes."

should read as follows:

--Identification of T-cell epitope sites using T-cell lines recognizing Cry j 1 revealed that the number of T-cell epitope sites recognized by each patient was 9.8 ± 3.0 on average and ranged from 4 ≤ 15 epitopes.--.

Col. 12, line 36, "Restriction molecules of each LHA class II type of T-cell clones whose restriction molecules were identified at the locus level can be identified by using, as antigen-presenting cells, mouse L-cells transformed with the DR gene and B-cell lines that are homozygous at the DQ or DP loci."

should read as follows:

--Restriction molecules of each HLA class II type of T-cell clones whose restriction molecules were identified at the locus level can be identified by using as antigen-presenting cells, mouse L-cells transformed with the DR gene and B-cell lines having the same DQ or DP haplotype.--.

Col. 13, line 7, "(Medojenics)" should be --(MedGenics)--.

Col. 55, Claim 1, line 48, "0501" should be --1501--.

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,025,964 B1 | |
| APPLICATION NO. | : 09/308027 | |
| DATED | : April 11, 2006 | |
| INVENTOR(S) | : Akinori Kume et al. | |

It is certified that error appears in the above-identified patent and that said Letters Patent is hereby corrected as shown below:

On the Title Page, Item 56 References Cited Section - OTHER PUBLICATIONS, line 4: "Janpanese" should be --Japanese--.

On the Title Page, Item 57
In the Abstract, lines 1-3: "A peptide-based inmunotherapeutic agent effective for every allergy patient is provided. A reagent for typing HLA class II molecules of the patient to be used in selecting a peptide-based immunotherapeutic agent effective for every allergy patient is also provided."

should read as follows:

--Peptide-based immunotherapeutic agents effective for each individual allergy patient are provided. Reagents for typing HLA class II molecules of patients to be used in selecting peptide-based immunotherapeutic agents effective for each individual allergy patient are also provided.--.

Col. 5, second paragraph, line 16, "challenge" should be --challenged--.

Col. 6, line 6, "to" should be --of--.

Col. 6, line 7, "allergy" should be--allergy.--.

Col. 6, line 7, "caused by antigen peptides presented by HLA-DPB1*0501. HLA-DPB1*0501 is frequently present in patients suffering from Cryptomeria pollen allergy induced by Cry j 1 and Cry j 2, and antigen peptides presented by different HLA class II molecules (DR.DQ or DP) (Japanese Patent Application No. Hei 8-70702)."

should read as follows:

--These multiple-epitope peptides comprise antigen peptides presented by different HLA class II molecules (DR, DQ or DP),and antigen peptides that are derived from both Cry j 1 and Cry j 2 and which are presented by HLA-DPB1*0501 (Japanese Patent Application No. Hei 8-80702). HLA-DPB1*0501 exists at a high frequency in patients suffering from cryptomeria pollen allergy.--

Col. 6, line 4, after "provided" please add --, for example,--.

Col. 6, line 5, "multiple" should be --multi--.

UNITED STATES PATENT AND TRADEMARK OFFICE
CERTIFICATE OF CORRECTION

PATENT NO. : 7,025,964 B1
APPLICATION NO. : 09/308027
DATED : April 11, 2006
INVENTOR(S) : Akinori Kume et al.

It is certified that error appears in the above-identified patent and that said Letters Patent is hereby corrected as shown below:

Col. 7, line 1, "there is a bias in the use of HLA class II (at the locus level) molecules that is determined by the antigen."

should read as follows:

--, depending on the antigen type, there is a bias towards restriction molecules at the HLA class II locus level, and that this defines immune reactions.--.

Col. 8, line 11, "Moreover, if T-cell response can be found in a subject (an allergic-response-positive patient), the type of the subject's HLA class II molecules restricting the antigen peptides that induced the T-cell response can be identified as the HLA class II type endowing susceptibility to said allergen in the subject."

should read as follows:

--For subjects showing a T cell response (allergy response-positive patients), the type of HLA class II restriction molecule for the antigen peptide that induces the T cell response can be identified as the subjects' HLA class II type.--.

Col. 8, line 65, "expression of a polypeptide with a peptide composed of"
should read as follows: --expressing, as a polypeptide, a peptide with--.

Col. 9, line 14, "shows the overlapping peptides of Cry j 1 containing epitopes recognized by patient's T-cells"

should read as follows: --shows Cry j 1 overlapping peptide sequences and the patients' T-cell epitope sites.--

Col. 9, line 18, "shows the overlapping peptides of Cry j 2 containing epitopes recognized by patient's T-cells"

should read as follows: --shows Cry j 2 overlapping peptides and the patients' T-cell epitope sites.--.

Col. 9, line 39, "shows the immune responses of CB6F1 mouse to Cry j 2 when the antigen peptide p186-200 of Cry j 2 was administered to the mouse."

should read as follows; --shows the immune response of CB6FI mice to Cry j 2 when the antigen peptide p236-250 of Cry j 2 was administered to the mice..--.

UNITED STATES PATENT AND TRADEMARK OFFICE
CERTIFICATE OF CORRECTION

PATENT NO. : 7,025,964 B1
APPLICATION NO. : 09/308027
DATED : April 11, 2006
INVENTOR(S) : Akinori Kume et al.

It is certified that error appears in the above-identified patent and that said Letters Patent is hereby corrected as shown below:

Col. 11, line 1, "The number of T-cell epitope sites of Cry j 1 recognized by each patient was 9.8 ± 3.0 on average and ranged from 4 = 15 epitopes."

should read as follows:

--Identification of T-cell epitope sites using T-cell lines recognizing Cry j 1 revealed that the number of T-cell epitope sites recognized by each patient was 9.8 ± 3.0 on average and ranged from 4 = 15 epitopes.--.

Col. 12, line 36, "Restriction molecules of each LHA class II type of T-cell clones whose restriction molecules were identified at the locus level can be identified by using, as antigen-presenting cells, mouse L-cells transformed with the DR gene and B-cell lines that are homozygous at the DQ or DP loci."

should read as follows:

--Restriction molecules of each HLA class II type of T-cell clones whose restriction molecules were identified at the locus level can be identified by using as antigen-presenting cells, mouse L-cells transformed with the DR gene and B-cell lines having the same DQ or DP haplotype.--.

Col. 13, line 7, "(Medojenics)" should be --(MedGenics)--.

Col. 55, Claim 1, line 48, "0501" should be --1501--.

This certificate supersedes Certificate of Correction issued December 12, 2006.

Signed and Sealed this

Third Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,025,964 B1
APPLICATION NO. : 09/308027
DATED : April 11, 2006
INVENTOR(S) : Akinori Kume et al.

It is certified that error appears in the above-identified patent and that said Letters Patent is hereby corrected as shown below:

On the Title Page, Item 56 References Cited Section - OTHER PUBLICATIONS, line 4: "Janpanese" should be --Japanese--.

On the Title Page, Item 57
In the Abstract, lines 1-3: "A peptide-based inmunotherapeutic agent effective for every allergy patient is provided. A reagent for typing HLA class II molecules of the patient to be used in selecting a peptide-based immunotherapeutic agent effective for every allergy patient is also provided."

should read as follows:

--Peptide-based immunotherapeutic agents effective for each individual allergy patient are provided. Reagents for typing HLA class II molecules of patients to be used in selecting peptide-based immunotherapeutic agents effective for each individual allergy patient are also provided.--.

Col. 5, second paragraph, line 16, "challenge" should be --challenged--.

Col. 6, line 6, "to" should be --of--.

Col. 6, line 7, "allergy" should be --allergy.--.

Col. 6, line 7, "caused by antigen peptides presented by HLA-DPB1*0501. HLA-DPB1*0501 is frequently present in patients suffering from Cryptomeria pollen allergy induced by Cry j 1 and Cry j 2, and antigen peptides presented by different HLA class II molecules (DR.DQ or DP) (Japanese Patent Application No. Hei 8-70702)."

should read as follows:

--These multiple-epitope peptides comprise antigen peptides presented by different HLA class II molecules (DR, DQ or DP),and antigen peptides that are derived from both Cry j 1 and Cry j 2 and which are presented by HLA-DPB1*0501 (Japanese Patent Application No. Hei 8-80702). HLA-DPB1*0501 exists at a high frequency in patients suffering from cryptomeria pollen allergy.--

Col. 6, line 4, after "provided" please add --, for example,--.

Col. 6, line 5, "multiple" should be --multi--.

UNITED STATES PATENT AND TRADEMARK OFFICE
CERTIFICATE OF CORRECTION

PATENT NO. : 7,025,964 B1
APPLICATION NO. : 09/308027
DATED : April 11, 2006
INVENTOR(S) : Akinori Kume et al.

It is certified that error appears in the above-identified patent and that said Letters Patent is hereby corrected as shown below:

Col. 7, line 1, "there is a bias in the use of HLA class II (at the locus level) molecules that is determined by the antigen."

should read as follows:

--, depending on the antigen type, there is a bias towards restriction molecules at the HLA class II locus level, and that this defines immune reactions.--.

Col. 8, line 11, "Moreover, if T-cell response can be found in a subject (an allergic-response-positive patient), the type of the subject's HLA class II molecules restricting the antigen peptides that induced the T-cell response can be identified as the HLA class II type endowing susceptibility to said allergen in the subject."

should read as follows:

--For subjects showing a T cell response (allergy response-positive patients), the type of HLA class II restriction molecule for the antigen peptide that induces the T cell response can be identified as the subjects' HLA class II type.--.

Col. 8, line 65, "expression of a polypeptide with a peptide composed of"
should read as follows: --expressing, as a polypeptide, a peptide with--.

Col. 9, line 14, "shows the overlapping peptides of Cry j 1 containing epitopes recognized by patient's T-cells"

should read as follows: --shows Cry j 1 overlapping peptide sequences and the patients' T-cell epitope sites.--

Col. 9, line 18, "shows the overlapping peptides of Cry j 2 containing epitopes recognized by patient's T-cells"

should read as follows: --shows Cry j 2 overlapping peptides and the patients' T-cell epitope sites.--.

Col. 9, line 39, "shows the immune responses of CB6F1 mouse to Cry j 2 when the antigen peptide p186-200 of Cry j 2 was administered to the mouse."

should read as follows; --shows the immune response of CB6FI mice to Cry j 2 when the antigen peptide p236-250 of Cry j 2 was administered to the mice..--.

UNITED STATES PATENT AND TRADEMARK OFFICE
CERTIFICATE OF CORRECTION

PATENT NO. : 7,025,964 B1
APPLICATION NO. : 09/308027
DATED : April 11, 2006
INVENTOR(S) : Akinori Kume et al.

It is certified that error appears in the above-identified patent and that said Letters Patent is hereby corrected as shown below:

Col. 11, line 1, "The number of T-cell epitope sites of Cry j 1 recognized by each patient was 9.8 ± 3.0 on average and ranged from 4 = 15 epitopes."

should read as follows:

--Identification of T-cell epitope sites using T-cell lines recognizing Cry j 1 revealed that the number of T-cell epitope sites recognized by each patient was 9.8 ± 3.0 on average and ranged from 4 = 15 epitopes.--.

Col. 12, line 36, "Restriction molecules of each LHA class II type of T-cell clones whose restriction molecules were identified at the locus level can be identified by using, as antigen-presenting cells, mouse L-cells transformed with the DR gene and B-cell lines that are homozygous at the DQ or DP loci."

should read as follows:

--Restriction molecules of each HLA class II type of T-cell clones whose restriction molecules were identified at the locus level can be identified by using as antigen-presenting cells, mouse L-cells transformed with the DR gene and B-cell lines having the same DQ or DP haplotype.--.

Col. 13, line 7, "(Medojenics)" should be --(MedGenics)--.

Col. 55, Claim 1, line 48, "0501" should be --1501--.

UNITED STATES PATENT AND TRADEMARK OFFICE
CERTIFICATE OF CORRECTION

| | | |
|---|---|---|
| PATENT NO. | : 7,025,964 B1 | |
| APPLICATION NO. | : 09/308027 | |
| DATED | : April 11, 2006 | |
| INVENTOR(S) | : Akinori Kume et al. | |

It is certified that error appears in the above-identified patent and that said Letters Patent is hereby corrected as shown below:

Col. 56, Claim 2, line 47, "0501" should be --1501--.

This certificate supersedes Certificates of Correction issued December 12, 2006 and April 3, 2007.

Signed and Sealed this

Third Day of July, 2007

JON W. DUDAS
*Director of the United States Patent and Trademark Office*

SEQUENCE LISTING

<160> NUMBER OF SEQ ID NOS: 146

<210> SEQ ID NO 1
<211> LENGTH: 15
<212> TYPE: PRT
<213> ORGANISM: Cryptomeria

<400> SEQUENCE: 1

Gln Asn Arg Met Lys Leu Ala Asp Cys Ala Val Gly Phe Gly Ser
 1               5                  10                  15

<210> SEQ ID NO 2
<211> LENGTH: 15
<212> TYPE: PRT
<213> ORGANISM: Cryptomeria

<400> SEQUENCE: 2

Gly Ala Thr Arg Asp Arg Pro Leu Trp Ile Ile Phe Ser Gly Asn
 1               5                  10                  15

<210> SEQ ID NO 3
<211> LENGTH: 15
<212> TYPE: PRT
<213> ORGANISM: Cryptomeria

<400> SEQUENCE: 3

Pro Cys Val Phe Ile Lys Arg Val Ser Asn Val Ile Ile His Gly
 1               5                  10                  15

<210> SEQ ID NO 4
<211> LENGTH: 9
<212> TYPE: PRT
<213> ORGANISM: Cryptomeria

<400> SEQUENCE: 4

Phe Ile Lys Arg Val Ser Asn Val Ile
 1               5

<210> SEQ ID NO 5
<211> LENGTH: 15
<212> TYPE: PRT
<213> ORGANISM: Cryptomeria

<400> SEQUENCE: 5

His Pro Gln Asp Gly Asp Ala Leu Thr Leu Arg Thr Ala Thr Asn
 1               5                  10                  15

<210> SEQ ID NO 6
<211> LENGTH: 15
<212> TYPE: PRT
<213> ORGANISM: Cryptomeria

<400> SEQUENCE: 6

Asp Ala Leu Thr Leu Arg Thr Ala Thr Asn Ile Trp Ile Asp His
 1               5                  10                  15

<210> SEQ ID NO 7
<211> LENGTH: 15
<212> TYPE: PRT
<213> ORGANISM: Cryptomeria

<400> SEQUENCE: 7

Leu Phe Phe Asn His His Lys Val Met Leu Leu Gly His Asp Asp
 1               5                  10                  15

```
<210> SEQ ID NO 8
<211> LENGTH: 15
<212> TYPE: PRT
<213> ORGANISM: Cryptomeria

<400> SEQUENCE: 8

Lys Ser Met Lys Val Thr Val Ala Phe Asn Gln Phe Gly Pro Asn
 1               5                  10                  15

<210> SEQ ID NO 9
<211> LENGTH: 15
<212> TYPE: PRT
<213> ORGANISM: Cryptomeria

<400> SEQUENCE: 9

Tyr Ala Ile Gly Gly Ser Ser Asn Pro Thr Ile Leu Ser Glu Gly
 1               5                  10                  15

<210> SEQ ID NO 10
<211> LENGTH: 15
<212> TYPE: PRT
<213> ORGANISM: Cryptomeria

<400> SEQUENCE: 10

Ala Phe Asn Val Glu Asn Gly Asn Ala Thr Pro Gln Leu Thr Lys
 1               5                  10                  15

<210> SEQ ID NO 11
<211> LENGTH: 11
<212> TYPE: PRT
<213> ORGANISM: Cryptomeria

<400> SEQUENCE: 11

Thr Pro Gln Leu Thr Lys Asn Ala Gly Val Leu
 1               5                  10

<210> SEQ ID NO 12
<211> LENGTH: 15
<212> TYPE: PRT
<213> ORGANISM: Cryptomeria

<400> SEQUENCE: 12

Gly Lys His Asp Cys Thr Glu Ala Phe Ser Thr Ala Trp Gln Ala
 1               5                  10                  15

<210> SEQ ID NO 13
<211> LENGTH: 15
<212> TYPE: PRT
<213> ORGANISM: Cryptomeria

<400> SEQUENCE: 13

Ser Ala Met Leu Leu Val Pro Gly Ser Lys Lys Phe Val Val Asn
 1               5                  10                  15

<210> SEQ ID NO 14
<211> LENGTH: 15
<212> TYPE: PRT
<213> ORGANISM: Cryptomeria

<400> SEQUENCE: 14

Val Asp Gly Ile Ile Ala Ala Tyr Gln Asn Pro Ala Ser Trp Lys
 1               5                  10                  15

<210> SEQ ID NO 15
```

```
<211> LENGTH: 15
<212> TYPE: PRT
<213> ORGANISM: Cryptomeria

<400> SEQUENCE: 15

Pro Ala Ser Trp Lys Asn Asn Arg Ile Trp Leu Gln Phe Ala Lys
 1               5                  10                  15

<210> SEQ ID NO 16
<211> LENGTH: 15
<212> TYPE: PRT
<213> ORGANISM: Cryptomeria

<400> SEQUENCE: 16

Pro Glu Phe His Leu Val Phe Gly Asn Cys Glu Gly Val Lys Ile
 1               5                  10                  15

<210> SEQ ID NO 17
<211> LENGTH: 15
<212> TYPE: PRT
<213> ORGANISM: Cryptomeria

<400> SEQUENCE: 17

Gly Ile Asp Ile Phe Ala Ser Lys Asn Phe His Leu Gln Lys Asn
 1               5                  10                  15

<210> SEQ ID NO 18
<211> LENGTH: 15
<212> TYPE: PRT
<213> ORGANISM: Cryptomeria

<400> SEQUENCE: 18

Ala Ser Lys Asn Phe His Leu Gln Lys Asn Thr Ile Gly Thr Gly
 1               5                  10                  15

<210> SEQ ID NO 19
<211> LENGTH: 15
<212> TYPE: PRT
<213> ORGANISM: Cryptomeria

<400> SEQUENCE: 19

Ser Arg Ala Glu Val Ser Tyr Val His Val Asn Gly Ala Lys Phe
 1               5                  10                  15

<210> SEQ ID NO 20
<211> LENGTH: 15
<212> TYPE: PRT
<213> ORGANISM: Cryptomeria

<400> SEQUENCE: 20

Ala Thr Ala Ala Ala Ile Gln Leu Lys Cys Ser Asp Ser Met Pro
 1               5                  10                  15

<210> SEQ ID NO 21
<211> LENGTH: 15
<212> TYPE: PRT
<213> ORGANISM: Cryptomeria

<400> SEQUENCE: 21

Ile Gln Leu Lys Cys Ser Asp Ser Met Pro Cys Lys Asp Ile Lys
 1               5                  10                  15

<210> SEQ ID NO 22
<211> LENGTH: 15
<212> TYPE: PRT
<213> ORGANISM: Cryptomeria
```

<400> SEQUENCE: 22

Cys Lys Asp Ile Lys Leu Ser Asp Ile Ser Leu Lys Leu Thr Ser
 1               5                  10                  15

<210> SEQ ID NO 23
<211> LENGTH: 15
<212> TYPE: PRT
<213> ORGANISM: Cryptomeria

<400> SEQUENCE: 23

Leu Ser Asp Ile Ser Leu Lys Leu Thr Ser Gly Lys Ile Ala Ser
 1               5                  10                  15

<210> SEQ ID NO 24
<211> LENGTH: 9
<212> TYPE: PRT
<213> ORGANISM: Cryptomeria

<400> SEQUENCE: 24

Lys Val Thr Val Ala Phe Asn Gln Phe
 1               5

<210> SEQ ID NO 25
<211> LENGTH: 15
<212> TYPE: PRT
<213> ORGANISM: Cryptomeria

<400> SEQUENCE: 25

Asp Asn Pro Ile Asp Ser Cys Trp Arg Gly Asp Ser Asn Trp Ala
 1               5                  10                  15

<210> SEQ ID NO 26
<211> LENGTH: 15
<212> TYPE: PRT
<213> ORGANISM: Cryptomeria

<400> SEQUENCE: 26

Ser Cys Trp Arg Gly Asp Ser Asn Trp Ala Gln Asn Arg Met Lys
 1               5                  10                  15

<210> SEQ ID NO 27
<211> LENGTH: 15
<212> TYPE: PRT
<213> ORGANISM: Cryptomeria

<400> SEQUENCE: 27

Asp Ser Asn Trp Ala Gln Asn Arg Met Lys Leu Ala Asp Cys Ala
 1               5                  10                  15

<210> SEQ ID NO 28
<211> LENGTH: 15
<212> TYPE: PRT
<213> ORGANISM: Cryptomeria

<400> SEQUENCE: 28

Leu Ala Asp Cys Ala Val Gly Phe Gly Ser Ser Thr Met Gly Gly
 1               5                  10                  15

<210> SEQ ID NO 29
<211> LENGTH: 15
<212> TYPE: PRT
<213> ORGANISM: Cryptomeria

<400> SEQUENCE: 29

Val Gly Phe Gly Ser Ser Thr Met Gly Lys Gly Gly Asp Leu
 1               5                  10                  15

<210> SEQ ID NO 30
<211> LENGTH: 15
<212> TYPE: PRT
<213> ORGANISM: Cryptomeria

<400> SEQUENCE: 30

Ser Thr Met Gly Gly Lys Gly Gly Asp Leu Tyr Thr Val Thr Asn
 1               5                  10                  15

<210> SEQ ID NO 31
<211> LENGTH: 15
<212> TYPE: PRT
<213> ORGANISM: Cryptomeria

<400> SEQUENCE: 31

Lys Gly Gly Asp Leu Tyr Thr Val Thr Asn Ser Asp Asp Pro
 1               5                  10                  15

<210> SEQ ID NO 32
<211> LENGTH: 15
<212> TYPE: PRT
<213> ORGANISM: Cryptomeria

<400> SEQUENCE: 32

Tyr Thr Val Thr Asn Ser Asp Asp Pro Val Asn Pro Ala Pro
 1               5                  10                  15

<210> SEQ ID NO 33
<211> LENGTH: 15
<212> TYPE: PRT
<213> ORGANISM: Cryptomeria

<400> SEQUENCE: 33

Ser Asp Asp Asp Pro Val Asn Pro Ala Pro Gly Thr Leu Arg Tyr
 1               5                  10                  15

<210> SEQ ID NO 34
<211> LENGTH: 15
<212> TYPE: PRT
<213> ORGANISM: Cryptomeria

<400> SEQUENCE: 34

Val Asn Pro Ala Pro Gly Thr Leu Arg Tyr Gly Ala Thr Arg Asp
 1               5                  10                  15

<210> SEQ ID NO 35
<211> LENGTH: 15
<212> TYPE: PRT
<213> ORGANISM: Cryptomeria

<400> SEQUENCE: 35

Gly Thr Leu Arg Tyr Gly Ala Thr Arg Asp Arg Pro Leu Trp Ile
 1               5                  10                  15

<210> SEQ ID NO 36
<211> LENGTH: 15
<212> TYPE: PRT
<213> ORGANISM: Cryptomeria

<400> SEQUENCE: 36

Arg Pro Leu Trp Ile Ile Phe Ser Gly Asn Met Asn Ile Lys Leu
 1               5                  10                  15

```
<210> SEQ ID NO 37
<211> LENGTH: 15
<212> TYPE: PRT
<213> ORGANISM: Cryptomeria

<400> SEQUENCE: 37

Ile Phe Ser Gly Asn Met Asn Ile Lys Leu Lys Met Pro Met Tyr
 1               5                  10                  15

<210> SEQ ID NO 38
<211> LENGTH: 15
<212> TYPE: PRT
<213> ORGANISM: Cryptomeria

<400> SEQUENCE: 38

Met Asn Ile Lys Leu Lys Met Pro Met Tyr Ile Ala Gly Tyr Lys
 1               5                  10                  15

<210> SEQ ID NO 39
<211> LENGTH: 15
<212> TYPE: PRT
<213> ORGANISM: Cryptomeria

<400> SEQUENCE: 39

Lys Met Pro Met Tyr Ile Ala Gly Tyr Lys Thr Phe Asp Gly Arg
 1               5                  10                  15

<210> SEQ ID NO 40
<211> LENGTH: 15
<212> TYPE: PRT
<213> ORGANISM: Cryptomeria

<400> SEQUENCE: 40

Ile Ala Gly Tyr Lys Thr Phe Asp Gly Arg Gly Ala Gln Val Tyr
 1               5                  10                  15

<210> SEQ ID NO 41
<211> LENGTH: 15
<212> TYPE: PRT
<213> ORGANISM: Cryptomeria

<400> SEQUENCE: 41

Thr Phe Asp Gly Arg Gly Ala Gln Val Tyr Ile Gly Asn Gly Gly
 1               5                  10                  15

<210> SEQ ID NO 42
<211> LENGTH: 15
<212> TYPE: PRT
<213> ORGANISM: Cryptomeria

<400> SEQUENCE: 42

Gly Ala Gln Val Tyr Ile Gly Asn Gly Gly Pro Cys Val Phe Ile
 1               5                  10                  15

<210> SEQ ID NO 43
<211> LENGTH: 15
<212> TYPE: PRT
<213> ORGANISM: Cryptomeria

<400> SEQUENCE: 43

Ile Gly Asn Gly Gly Pro Cys Val Phe Ile Lys Arg Val Ser Asn
 1               5                  10                  15

<210> SEQ ID NO 44
<211> LENGTH: 15
```

```
<212> TYPE: PRT
<213> ORGANISM: Cryptomeria

<400> SEQUENCE: 44

Lys Arg Val Ser Asn Val Ile Ile His Gly Leu His Leu Tyr Gly
 1               5                  10                  15

<210> SEQ ID NO 45
<211> LENGTH: 15
<212> TYPE: PRT
<213> ORGANISM: Cryptomeria

<400> SEQUENCE: 45

Val Ile Ile His Gly Leu His Leu Tyr Gly Cys Ser Thr Ser Val
 1               5                  10                  15

<210> SEQ ID NO 46
<211> LENGTH: 15
<212> TYPE: PRT
<213> ORGANISM: Cryptomeria

<400> SEQUENCE: 46

Leu His Leu Tyr Gly Cys Ser Thr Ser Val Leu Gly Asn Val Leu
 1               5                  10                  15

<210> SEQ ID NO 47
<211> LENGTH: 15
<212> TYPE: PRT
<213> ORGANISM: Cryptomeria

<400> SEQUENCE: 47

Cys Ser Thr Ser Val Leu Gly Asn Val Leu Ile Asn Glu Ser Phe
 1               5                  10                  15

<210> SEQ ID NO 48
<211> LENGTH: 15
<212> TYPE: PRT
<213> ORGANISM: Cryptomeria

<400> SEQUENCE: 48

Leu Gly Asn Val Leu Ile Asn Glu Ser Phe Gly Val Glu Pro Val
 1               5                  10                  15

<210> SEQ ID NO 49
<211> LENGTH: 15
<212> TYPE: PRT
<213> ORGANISM: Cryptomeria

<400> SEQUENCE: 49

Ile Asn Glu Ser Phe Gly Val Glu Pro Val His Pro Gln Asp Gly
 1               5                  10                  15

<210> SEQ ID NO 50
<211> LENGTH: 15
<212> TYPE: PRT
<213> ORGANISM: Cryptomeria

<400> SEQUENCE: 50

Gly Val Glu Pro Val His Pro Gln Asp Gly Asp Ala Leu Thr Leu
 1               5                  10                  15

<210> SEQ ID NO 51
<211> LENGTH: 15
<212> TYPE: PRT
<213> ORGANISM: Cryptomeria
```

```
<400> SEQUENCE: 51

Arg Thr Ala Thr Asn Ile Trp Ile Asp His Asn Ser Phe Ser Asn
 1               5                  10                  15

<210> SEQ ID NO 52
<211> LENGTH: 15
<212> TYPE: PRT
<213> ORGANISM: Cryptomeria

<400> SEQUENCE: 52

Ile Trp Ile Asp His Asn Ser Phe Ser Asn Ser Ser Asp Gly Leu
 1               5                  10                  15

<210> SEQ ID NO 53
<211> LENGTH: 15
<212> TYPE: PRT
<213> ORGANISM: Cryptomeria

<400> SEQUENCE: 53

Asn Ser Phe Ser Asn Ser Ser Asp Gly Leu Val Asp Val Thr Leu
 1               5                  10                  15

<210> SEQ ID NO 54
<211> LENGTH: 15
<212> TYPE: PRT
<213> ORGANISM: Cryptomeria

<400> SEQUENCE: 54

Ser Ser Asp Gly Leu Val Asp Val Thr Leu Ser Ser Thr Gly Val
 1               5                  10                  15

<210> SEQ ID NO 55
<211> LENGTH: 15
<212> TYPE: PRT
<213> ORGANISM: Cryptomeria

<400> SEQUENCE: 55

Val Asp Val Thr Leu Ser Ser Thr Gly Val Thr Ile Ser Asn Asn
 1               5                  10                  15

<210> SEQ ID NO 56
<211> LENGTH: 15
<212> TYPE: PRT
<213> ORGANISM: Cryptomeria

<400> SEQUENCE: 56

Ser Ser Thr Gly Val Thr Ile Ser Asn Asn Leu Phe Phe Asn His
 1               5                  10                  15

<210> SEQ ID NO 57
<211> LENGTH: 15
<212> TYPE: PRT
<213> ORGANISM: Cryptomeria

<400> SEQUENCE: 57

Thr Ile Ser Asn Asn Leu Phe Phe Asn His His Lys Val Met Leu
 1               5                  10                  15

<210> SEQ ID NO 58
<211> LENGTH: 15
<212> TYPE: PRT
<213> ORGANISM: Cryptomeria

<400> SEQUENCE: 58

His Lys Val Met Leu Leu Gly His Asp Asp Ala Tyr Ser Asp Asp
```

```
<210> SEQ ID NO 59
<211> LENGTH: 15
<212> TYPE: PRT
<213> ORGANISM: Cryptomeria

<400> SEQUENCE: 59

Leu Gly His Asp Asp Ala Tyr Ser Asp Asp Lys Ser Met Lys Val
 1               5                  10                  15

<210> SEQ ID NO 60
<211> LENGTH: 15
<212> TYPE: PRT
<213> ORGANISM: Cryptomeria

<400> SEQUENCE: 60

Ala Tyr Ser Asp Asp Lys Ser Met Lys Val Thr Val Ala Phe Asn
 1               5                  10                  15

<210> SEQ ID NO 61
<211> LENGTH: 15
<212> TYPE: PRT
<213> ORGANISM: Cryptomeria

<400> SEQUENCE: 61

Thr Val Ala Phe Asn Gln Phe Gly Pro Asn Cys Gly Gln Arg Met
 1               5                  10                  15

<210> SEQ ID NO 62
<211> LENGTH: 15
<212> TYPE: PRT
<213> ORGANISM: Cryptomeria

<400> SEQUENCE: 62

Gln Phe Gly Pro Asn Cys Gly Gln Arg Met Pro Arg Ala Arg Tyr
 1               5                  10                  15

<210> SEQ ID NO 63
<211> LENGTH: 15
<212> TYPE: PRT
<213> ORGANISM: Cryptomeria

<400> SEQUENCE: 63

Cys Gly Gln Arg Met Pro Arg Ala Arg Tyr Gly Leu Val His Val
 1               5                  10                  15

<210> SEQ ID NO 64
<211> LENGTH: 15
<212> TYPE: PRT
<213> ORGANISM: Cryptomeria

<400> SEQUENCE: 64

Pro Arg Ala Arg Tyr Gly Leu Val His Val Ala Asn Asn Asn Tyr
 1               5                  10                  15

<210> SEQ ID NO 65
<211> LENGTH: 15
<212> TYPE: PRT
<213> ORGANISM: Cryptomeria

<400> SEQUENCE: 65

Gly Leu Val His Val Ala Asn Asn Asn Tyr Asp Pro Trp Thr Ile
 1               5                  10                  15
```

```
<210> SEQ ID NO 66
<211> LENGTH: 15
<212> TYPE: PRT
<213> ORGANISM: Cryptomeria

<400> SEQUENCE: 66

Ala Asn Asn Asn Tyr Asp Pro Trp Thr Ile Tyr Ala Ile Gly Gly
 1               5                  10                  15

<210> SEQ ID NO 67
<211> LENGTH: 15
<212> TYPE: PRT
<213> ORGANISM: Cryptomeria

<400> SEQUENCE: 67

Asp Pro Trp Thr Ile Tyr Ala Ile Gly Gly Ser Ser Asn Pro Thr
 1               5                  10                  15

<210> SEQ ID NO 68
<211> LENGTH: 15
<212> TYPE: PRT
<213> ORGANISM: Cryptomeria

<400> SEQUENCE: 68

Ser Ser Asn Pro Thr Ile Leu Ser Glu Gly Asn Ser Phe Thr Ala
 1               5                  10                  15

<210> SEQ ID NO 69
<211> LENGTH: 15
<212> TYPE: PRT
<213> ORGANISM: Cryptomeria

<400> SEQUENCE: 69

Ile Leu Ser Glu Gly Asn Ser Phe Thr Ala Pro Asn Glu Ser Tyr
 1               5                  10                  15

<210> SEQ ID NO 70
<211> LENGTH: 15
<212> TYPE: PRT
<213> ORGANISM: Cryptomeria

<400> SEQUENCE: 70

Asn Ser Phe Thr Ala Pro Asn Glu Ser Tyr Lys Lys Gln Val Thr
 1               5                  10                  15

<210> SEQ ID NO 71
<211> LENGTH: 15
<212> TYPE: PRT
<213> ORGANISM: Cryptomeria

<400> SEQUENCE: 71

Pro Asn Glu Ser Tyr Lys Lys Gln Val Thr Ile Arg Ile Gly Cys
 1               5                  10                  15

<210> SEQ ID NO 72
<211> LENGTH: 15
<212> TYPE: PRT
<213> ORGANISM: Cryptomeria

<400> SEQUENCE: 72

Lys Lys Gln Val Thr Ile Arg Ile Gly Cys Lys Thr Ser Ser Ser
 1               5                  10                  15

<210> SEQ ID NO 73
<211> LENGTH: 15
<212> TYPE: PRT
```

<213> ORGANISM: Cryptomeria

<400> SEQUENCE: 73

Ile Arg Ile Gly Cys Lys Thr Ser Ser Cys Ser Asn Trp Val
1               5                   10                  15

<210> SEQ ID NO 74
<211> LENGTH: 15
<212> TYPE: PRT
<213> ORGANISM: Cryptomeria

<400> SEQUENCE: 74

Lys Thr Ser Ser Ser Cys Ser Asn Trp Val Trp Gln Ser Thr Gln
1               5                   10                  15

<210> SEQ ID NO 75
<211> LENGTH: 15
<212> TYPE: PRT
<213> ORGANISM: Cryptomeria

<400> SEQUENCE: 75

Cys Ser Asn Trp Val Trp Gln Ser Thr Gln Asp Val Phe Tyr Asn
1               5                   10                  15

<210> SEQ ID NO 76
<211> LENGTH: 15
<212> TYPE: PRT
<213> ORGANISM: Cryptomeria

<400> SEQUENCE: 76

Trp Gln Ser Thr Gln Asp Val Phe Tyr Asn Gly Ala Tyr Phe Val
1               5                   10                  15

<210> SEQ ID NO 77
<211> LENGTH: 15
<212> TYPE: PRT
<213> ORGANISM: Cryptomeria

<400> SEQUENCE: 77

Asp Val Phe Tyr Asn Gly Ala Tyr Phe Val Ser Ser Gly Lys Tyr
1               5                   10                  15

<210> SEQ ID NO 78
<211> LENGTH: 15
<212> TYPE: PRT
<213> ORGANISM: Cryptomeria

<400> SEQUENCE: 78

Gly Ala Tyr Phe Val Ser Ser Gly Lys Tyr Glu Gly Gly Asn Ile
1               5                   10                  15

<210> SEQ ID NO 79
<211> LENGTH: 15
<212> TYPE: PRT
<213> ORGANISM: Cryptomeria

<400> SEQUENCE: 79

Ser Ser Gly Lys Tyr Glu Gly Gly Asn Ile Tyr Thr Lys Lys Glu
1               5                   10                  15

<210> SEQ ID NO 80
<211> LENGTH: 15
<212> TYPE: PRT
<213> ORGANISM: Cryptomeria

<400> SEQUENCE: 80

```
Glu Gly Gly Asn Ile Tyr Thr Lys Lys Glu Ala Phe Asn Val Glu
 1               5                  10                  15

<210> SEQ ID NO 81
<211> LENGTH: 15
<212> TYPE: PRT
<213> ORGANISM: Cryptomeria

<400> SEQUENCE: 81

Tyr Thr Lys Lys Glu Ala Phe Asn Val Glu Asn Gly Asn Ala Thr
 1               5                  10                  15

<210> SEQ ID NO 82
<211> LENGTH: 15
<212> TYPE: PRT
<213> ORGANISM: Cryptomeria

<400> SEQUENCE: 82

Asn Gly Asn Ala Thr Pro Gln Leu Thr Lys Asn Ala Gly Val Leu
 1               5                  10                  15

<210> SEQ ID NO 83
<211> LENGTH: 15
<212> TYPE: PRT
<213> ORGANISM: Cryptomeria

<400> SEQUENCE: 83

Pro Gln Leu Thr Lys Asn Ala Gly Val Leu Thr Cys Ser Leu Ser
 1               5                  10                  15

<210> SEQ ID NO 84
<211> LENGTH: 15
<212> TYPE: PRT
<213> ORGANISM: Cryptomeria

<400> SEQUENCE: 84

Thr Lys Asn Ala Gly Val Leu Thr Cys Ser Leu Ser Lys Arg Cys
 1               5                  10                  15

<210> SEQ ID NO 85
<211> LENGTH: 15
<212> TYPE: PRT
<213> ORGANISM: Cryptomeria

<400> SEQUENCE: 85

Ala Ile Asn Ile Phe Asn Val Glu Lys Tyr Gly Ala Val Gly Asp
 1               5                  10                  15

<210> SEQ ID NO 86
<211> LENGTH: 15
<212> TYPE: PRT
<213> ORGANISM: Cryptomeria

<400> SEQUENCE: 86

Asn Val Glu Lys Tyr Gly Ala Val Gly Asp Gly Lys His Asp Cys
 1               5                  10                  15

<210> SEQ ID NO 87
<211> LENGTH: 15
<212> TYPE: PRT
<213> ORGANISM: Cryptomeria

<400> SEQUENCE: 87

Gly Ala Val Gly Asp Gly Lys His Asp Cys Thr Glu Ala Phe Ser
 1               5                  10                  15
```

<210> SEQ ID NO 88
<211> LENGTH: 15
<212> TYPE: PRT
<213> ORGANISM: Cryptomeria

<400> SEQUENCE: 88

Thr Glu Ala Phe Ser Thr Ala Trp Gln Ala Ala Cys Lys Asn Pro
 1               5                  10                  15

<210> SEQ ID NO 89
<211> LENGTH: 15
<212> TYPE: PRT
<213> ORGANISM: Cryptomeria

<400> SEQUENCE: 89

Thr Ala Trp Gln Ala Ala Cys Lys Asn Pro Ser Ala Met Leu Leu
 1               5                  10                  15

<210> SEQ ID NO 90
<211> LENGTH: 15
<212> TYPE: PRT
<213> ORGANISM: Cryptomeria

<400> SEQUENCE: 90

Ala Cys Lys Asn Pro Ser Ala Met Leu Leu Val Pro Gly Ser Lys
 1               5                  10                  15

<210> SEQ ID NO 91
<211> LENGTH: 15
<212> TYPE: PRT
<213> ORGANISM: Cryptomeria

<400> SEQUENCE: 91

Val Pro Gly Ser Lys Lys Phe Val Val Asn Asn Leu Phe Phe Asn
 1               5                  10                  15

<210> SEQ ID NO 92
<211> LENGTH: 15
<212> TYPE: PRT
<213> ORGANISM: Cryptomeria

<400> SEQUENCE: 92

Lys Phe Val Val Asn Asn Leu Phe Phe Asn Gly Pro Cys Gln Pro
 1               5                  10                  15

<210> SEQ ID NO 93
<211> LENGTH: 15
<212> TYPE: PRT
<213> ORGANISM: Cryptomeria

<400> SEQUENCE: 93

Asn Leu Phe Phe Asn Gly Pro Cys Gln Pro His Phe Thr Phe Lys
 1               5                  10                  15

<210> SEQ ID NO 94
<211> LENGTH: 15
<212> TYPE: PRT
<213> ORGANISM: Cryptomeria

<400> SEQUENCE: 94

Gly Pro Cys Gln Pro His Phe Thr Phe Lys Val Asp Gly Ile Ile
 1               5                  10                  15

<210> SEQ ID NO 95

<211> LENGTH: 15
<212> TYPE: PRT
<213> ORGANISM: Cryptomeria

<400> SEQUENCE: 95

His Phe Thr Phe Lys Val Asp Gly Ile Ile Ala Ala Tyr Gln Asn
 1               5                  10                  15

<210> SEQ ID NO 96
<211> LENGTH: 15
<212> TYPE: PRT
<213> ORGANISM: Cryptomeria

<400> SEQUENCE: 96

Ala Ala Tyr Gln Asn Pro Ala Ser Trp Lys Asn Asn Arg Ile Trp
 1               5                  10                  15

<210> SEQ ID NO 97
<211> LENGTH: 15
<212> TYPE: PRT
<213> ORGANISM: Cryptomeria

<400> SEQUENCE: 97

Asn Asn Arg Ile Trp Leu Gln Phe Ala Lys Leu Thr Gly Phe Thr
 1               5                  10                  15

<210> SEQ ID NO 98
<211> LENGTH: 15
<212> TYPE: PRT
<213> ORGANISM: Cryptomeria

<400> SEQUENCE: 98

Leu Gln Phe Ala Lys Leu Thr Gly Phe Thr Leu Met Gly Lys Gly
 1               5                  10                  15

<210> SEQ ID NO 99
<211> LENGTH: 15
<212> TYPE: PRT
<213> ORGANISM: Cryptomeria

<400> SEQUENCE: 99

Leu Thr Gly Phe Thr Leu Met Gly Lys Gly Val Ile Asp Gly Gln
 1               5                  10                  15

<210> SEQ ID NO 100
<211> LENGTH: 15
<212> TYPE: PRT
<213> ORGANISM: Cryptomeria

<400> SEQUENCE: 100

Leu Met Gly Lys Gly Val Ile Asp Gly Gln Gly Lys Gln Trp Trp
 1               5                  10                  15

<210> SEQ ID NO 101
<211> LENGTH: 15
<212> TYPE: PRT
<213> ORGANISM: Cryptomeria

<400> SEQUENCE: 101

Val Ile Asp Gly Gln Gly Lys Gln Trp Trp Ala Gly Gln Cys Lys
 1               5                  10                  15

<210> SEQ ID NO 102
<211> LENGTH: 15
<212> TYPE: PRT
<213> ORGANISM: Cryptomeria

<400> SEQUENCE: 102

Gly Lys Gln Trp Trp Ala Gly Gln Cys Lys Trp Val Asn Gly Arg
 1               5                  10                  15

<210> SEQ ID NO 103
<211> LENGTH: 15
<212> TYPE: PRT
<213> ORGANISM: Cryptomeria

<400> SEQUENCE: 103

Ala Gly Gln Cys Lys Trp Val Asn Gly Arg Glu Ile Cys Asn Asp
 1               5                  10                  15

<210> SEQ ID NO 104
<211> LENGTH: 15
<212> TYPE: PRT
<213> ORGANISM: Cryptomeria

<400> SEQUENCE: 104

Trp Val Asn Gly Arg Glu Ile Cys Asn Asp Arg Asp Arg Pro Thr
 1               5                  10                  15

<210> SEQ ID NO 105
<211> LENGTH: 15
<212> TYPE: PRT
<213> ORGANISM: Cryptomeria

<400> SEQUENCE: 105

Glu Ile Cys Asn Asp Arg Asp Arg Pro Thr Ala Ile Lys Phe Asp
 1               5                  10                  15

<210> SEQ ID NO 106
<211> LENGTH: 15
<212> TYPE: PRT
<213> ORGANISM: Cryptomeria

<400> SEQUENCE: 106

Arg Asp Arg Pro Thr Ala Ile Lys Phe Asp Phe Ser Thr Gly Leu
 1               5                  10                  15

<210> SEQ ID NO 107
<211> LENGTH: 15
<212> TYPE: PRT
<213> ORGANISM: Cryptomeria

<400> SEQUENCE: 107

Ala Ile Lys Phe Asp Phe Ser Thr Gly Leu Ile Ile Gln Gly Leu
 1               5                  10                  15

<210> SEQ ID NO 108
<211> LENGTH: 15
<212> TYPE: PRT
<213> ORGANISM: Cryptomeria

<400> SEQUENCE: 108

Phe Ser Thr Gly Leu Ile Ile Gln Gly Leu Lys Leu Met Asn Ser
 1               5                  10                  15

<210> SEQ ID NO 109
<211> LENGTH: 15
<212> TYPE: PRT
<213> ORGANISM: Cryptomeria

<400> SEQUENCE: 109

Ile Ile Gln Gly Leu Lys Leu Met Asn Ser Pro Glu Phe His Leu
1               5                   10                  15

<210> SEQ ID NO 110
<211> LENGTH: 15
<212> TYPE: PRT
<213> ORGANISM: Cryptomeria

<400> SEQUENCE: 110

Lys Leu Met Asn Ser Pro Glu Phe His Leu Val Phe Gly Asn Cys
1               5                   10                  15

<210> SEQ ID NO 111
<211> LENGTH: 15
<212> TYPE: PRT
<213> ORGANISM: Cryptomeria

<400> SEQUENCE: 111

Val Phe Gly Asn Cys Glu Gly Val Lys Ile Ile Gly Ile Ser Ile
1               5                   10                  15

<210> SEQ ID NO 112
<211> LENGTH: 15
<212> TYPE: PRT
<213> ORGANISM: Cryptomeria

<400> SEQUENCE: 112

Glu Gly Val Lys Ile Ile Gly Ile Ser Ile Thr Ala Pro Arg Asp
1               5                   10                  15

<210> SEQ ID NO 113
<211> LENGTH: 15
<212> TYPE: PRT
<213> ORGANISM: Cryptomeria

<400> SEQUENCE: 113

Ile Gly Ile Ser Ile Thr Ala Pro Arg Asp Ser Pro Asn Thr Asp
1               5                   10                  15

<210> SEQ ID NO 114
<211> LENGTH: 15
<212> TYPE: PRT
<213> ORGANISM: Cryptomeria

<400> SEQUENCE: 114

Thr Ala Pro Arg Asp Ser Pro Asn Thr Asp Gly Ile Asp Ile Phe
1               5                   10                  15

<210> SEQ ID NO 115
<211> LENGTH: 15
<212> TYPE: PRT
<213> ORGANISM: Cryptomeria

<400> SEQUENCE: 115

Ser Pro Asn Thr Asp Gly Ile Asp Ile Phe Ala Ser Lys Asn Phe
1               5                   10                  15

<210> SEQ ID NO 116
<211> LENGTH: 15
<212> TYPE: PRT
<213> ORGANISM: Cryptomeria

<400> SEQUENCE: 116

His Leu Gln Lys Asn Thr Ile Gly Thr Gly Asp Asp Cys Val Ala
1               5                   10                  15

```
<210> SEQ ID NO 117
<211> LENGTH: 15
<212> TYPE: PRT
<213> ORGANISM: Cryptomeria

<400> SEQUENCE: 117

Thr Ile Gly Thr Gly Asp Asp Cys Val Ala Ile Gly Thr Gly Ser
 1               5                  10                  15

<210> SEQ ID NO 118
<211> LENGTH: 15
<212> TYPE: PRT
<213> ORGANISM: Cryptomeria

<400> SEQUENCE: 118

Asp Asp Cys Val Ala Ile Gly Thr Gly Ser Ser Asn Ile Val Ile
 1               5                  10                  15

<210> SEQ ID NO 119
<211> LENGTH: 15
<212> TYPE: PRT
<213> ORGANISM: Cryptomeria

<400> SEQUENCE: 119

Ile Gly Thr Gly Ser Ser Asn Ile Val Ile Glu Asp Leu Ile Cys
 1               5                  10                  15

<210> SEQ ID NO 120
<211> LENGTH: 15
<212> TYPE: PRT
<213> ORGANISM: Cryptomeria

<400> SEQUENCE: 120

Ser Asn Ile Val Ile Glu Asp Leu Ile Cys Gly Pro Gly His Gly
 1               5                  10                  15

<210> SEQ ID NO 121
<211> LENGTH: 15
<212> TYPE: PRT
<213> ORGANISM: Cryptomeria

<400> SEQUENCE: 121

Glu Asp Leu Ile Cys Gly Pro Gly His Gly Ile Ser Ile Gly Ser
 1               5                  10                  15

<210> SEQ ID NO 122
<211> LENGTH: 15
<212> TYPE: PRT
<213> ORGANISM: Cryptomeria

<400> SEQUENCE: 122

Gly Pro Gly His Gly Ile Ser Ile Gly Ser Leu Gly Arg Glu Asn
 1               5                  10                  15

<210> SEQ ID NO 123
<211> LENGTH: 15
<212> TYPE: PRT
<213> ORGANISM: Cryptomeria

<400> SEQUENCE: 123

Ile Ser Ile Gly Ser Leu Gly Arg Glu Asn Ser Arg Ala Glu Val
 1               5                  10                  15

<210> SEQ ID NO 124
<211> LENGTH: 15
```

-continued

<210> SEQ ID NO 124 (implied)
<212> TYPE: PRT
<213> ORGANISM: Cryptomeria

<400> SEQUENCE: 124

Leu Gly Arg Glu Asn Ser Arg Ala Glu Val Ser Tyr Val His Val
 1               5                  10                  15

<210> SEQ ID NO 125
<211> LENGTH: 15
<212> TYPE: PRT
<213> ORGANISM: Cryptomeria

<400> SEQUENCE: 125

Ser Tyr Val His Val Asn Gly Ala Lys Phe Ile Asp Thr Gln Asn
 1               5                  10                  15

<210> SEQ ID NO 126
<211> LENGTH: 15
<212> TYPE: PRT
<213> ORGANISM: Cryptomeria

<400> SEQUENCE: 126

Asn Gly Ala Lys Phe Ile Asp Thr Gln Asn Gly Leu Arg Ile Lys
 1               5                  10                  15

<210> SEQ ID NO 127
<211> LENGTH: 15
<212> TYPE: PRT
<213> ORGANISM: Cryptomeria

<400> SEQUENCE: 127

Ile Asp Thr Gln Asn Gly Leu Arg Ile Lys Thr Trp Gln Gly Gly
 1               5                  10                  15

<210> SEQ ID NO 128
<211> LENGTH: 15
<212> TYPE: PRT
<213> ORGANISM: Cryptomeria

<400> SEQUENCE: 128

Gly Leu Arg Ile Lys Thr Trp Gln Gly Gly Ser Gly Met Ala Ser
 1               5                  10                  15

<210> SEQ ID NO 129
<211> LENGTH: 15
<212> TYPE: PRT
<213> ORGANISM: Cryptomeria

<400> SEQUENCE: 129

Thr Trp Gln Gly Gly Ser Gly Met Ala Ser His Ile Ile Tyr Glu
 1               5                  10                  15

<210> SEQ ID NO 130
<211> LENGTH: 15
<212> TYPE: PRT
<213> ORGANISM: Cryptomeria

<400> SEQUENCE: 130

Ser Gly Met Ala Ser His Ile Ile Tyr Glu Asn Val Glu Met Ile
 1               5                  10                  15

<210> SEQ ID NO 131
<211> LENGTH: 15
<212> TYPE: PRT
<213> ORGANISM: Cryptomeria

```
<400> SEQUENCE: 131

His Ile Ile Tyr Glu Asn Val Glu Met Ile Asn Ser Glu Asn Pro
 1               5                  10                  15

<210> SEQ ID NO 132
<211> LENGTH: 15
<212> TYPE: PRT
<213> ORGANISM: Cryptomeria

<400> SEQUENCE: 132

Asn Val Glu Met Ile Asn Ser Glu Asn Pro Ile Leu Ile Asn Gln
 1               5                  10                  15

<210> SEQ ID NO 133
<211> LENGTH: 15
<212> TYPE: PRT
<213> ORGANISM: Cryptomeria

<400> SEQUENCE: 133

Asn Ser Glu Asn Pro Ile Leu Ile Asn Gln Phe Tyr Cys Thr Ser
 1               5                  10                  15

<210> SEQ ID NO 134
<211> LENGTH: 15
<212> TYPE: PRT
<213> ORGANISM: Cryptomeria

<400> SEQUENCE: 134

Ile Leu Ile Asn Gln Phe Tyr Cys Thr Ser Ala Ser Ala Cys Gln
 1               5                  10                  15

<210> SEQ ID NO 135
<211> LENGTH: 15
<212> TYPE: PRT
<213> ORGANISM: Cryptomeria

<400> SEQUENCE: 135

Phe Tyr Cys Thr Ser Ala Ser Ala Cys Gln Asn Gln Arg Ser Ala
 1               5                  10                  15

<210> SEQ ID NO 136
<211> LENGTH: 15
<212> TYPE: PRT
<213> ORGANISM: Cryptomeria

<400> SEQUENCE: 136

Ala Ser Ala Cys Gln Asn Gln Arg Ser Ala Val Gln Ile Gln Asp
 1               5                  10                  15

<210> SEQ ID NO 137
<211> LENGTH: 15
<212> TYPE: PRT
<213> ORGANISM: Cryptomeria

<400> SEQUENCE: 137

Asn Gln Arg Ser Ala Val Gln Ile Gln Asp Val Thr Tyr Lys Asn
 1               5                  10                  15

<210> SEQ ID NO 138
<211> LENGTH: 15
<212> TYPE: PRT
<213> ORGANISM: Cryptomeria

<400> SEQUENCE: 138

Val Gln Ile Gln Asp Val Thr Tyr Lys Asn Ile Arg Gly Thr Ser
```

<210> SEQ ID NO 139
<211> LENGTH: 15
<212> TYPE: PRT
<213> ORGANISM: Cryptomeria

<400> SEQUENCE: 139

Val Thr Tyr Lys Asn Ile Arg Gly Thr Ser Ala Thr Ala Ala Ala
1               5                   10                  15

<210> SEQ ID NO 140
<211> LENGTH: 15
<212> TYPE: PRT
<213> ORGANISM: Cryptomeria

<400> SEQUENCE: 140

Ile Arg Gly Thr Ser Ala Thr Ala Ala Ala Ile Gln Leu Lys Cys
1               5                   10                  15

<210> SEQ ID NO 141
<211> LENGTH: 15
<212> TYPE: PRT
<213> ORGANISM: Cryptomeria

<400> SEQUENCE: 141

Ser Asp Ser Met Pro Cys Lys Asp Ile Lys Leu Ser Asp Ile Ser
1               5                   10                  15

<210> SEQ ID NO 142
<211> LENGTH: 15
<212> TYPE: PRT
<213> ORGANISM: Cryptomeria

<400> SEQUENCE: 142

Leu Lys Leu Thr Ser Gly Lys Ile Ala Ser Cys Leu Asn Asp Asn
1               5                   10                  15

<210> SEQ ID NO 143
<211> LENGTH: 15
<212> TYPE: PRT
<213> ORGANISM: Cryptomeria

<400> SEQUENCE: 143

Gly Lys Ile Ala Ser Cys Leu Asn Asp Asn Ala Asn Gly Tyr Phe
1               5                   10                  15

<210> SEQ ID NO 144
<211> LENGTH: 15
<212> TYPE: PRT
<213> ORGANISM: Cryptomeria

<400> SEQUENCE: 144

Cys Leu Asn Asp Asn Ala Asn Gly Tyr Phe Ser Gly His Val Ile
1               5                   10                  15

<210> SEQ ID NO 145
<211> LENGTH: 15
<212> TYPE: PRT
<213> ORGANISM: Cryptomeria

<400> SEQUENCE: 145

Ala Asn Gly Tyr Phe Ser Gly His Val Ile Pro Ala Cys Lys Asn
1               5                   10                  15

```
<210> SEQ ID NO 146
<211> LENGTH: 15
<212> TYPE: PRT
<213> ORGANISM: Cryptomeria

<400> SEQUENCE: 146

Ser Gly His Val Ile Pro Ala Cys Lys Asn Leu Ser Pro Ser Ala
 1               5                  10                  15
```